(12) United States Patent
Kuduvalli

(10) Patent No.: US 8,093,572 B2
(45) Date of Patent: Jan. 10, 2012

(54) INTEGRATED VARIABLE-APERTURE COLLIMATOR AND FIXED-APERTURE COLLIMATOR

(75) Inventor: Gopinath R. Kuduvalli, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 402 days.

(21) Appl. No.: 11/824,083

(22) Filed: Jun. 29, 2007

(65) Prior Publication Data

US 2009/0001296 A1  Jan. 1, 2009

(51) Int. Cl.
*G21K 1/02* (2006.01)

(52) U.S. Cl. ............ 250/505.1; 250/492.1; 378/65; 378/145; 378/147; 378/149; 378/150

(58) Field of Classification Search ........... 250/505.1, 250/492.1; 378/147, 150, 65, 145, 149, 151; 396/505–543
See application file for complete search history.

(56) References Cited

U.S. PATENT DOCUMENTS

| | | | |
|---|---|---|---|
| 2,675,486 A | | 4/1954 | Green et al. |
| 2,844,736 A | * | 7/1958 | Johns et al. ............ 378/152 |
| 2,959,680 A | * | 11/1960 | Green ................. 378/152 |
| 2,998,526 A | * | 8/1961 | Green et al. ............ 378/147 |
| 3,849,649 A | * | 11/1974 | Carey ................. 378/150 |
| 4,055,770 A | * | 10/1977 | Milcamps et al. ........ 378/153 |
| 4,086,494 A | * | 4/1978 | Malak ................ 378/153 |
| 4,143,273 A | | 3/1979 | Richey et al. |
| 4,145,616 A | * | 3/1979 | Tanabe ............... 378/150 |
| 4,359,642 A | * | 11/1982 | Heinz et al. ............ 378/150 |
| 4,450,578 A | | 5/1984 | Hill |
| 4,463,266 A | * | 7/1984 | Brahme .............. 250/505.1 |
| 4,489,426 A | * | 12/1984 | Grass et al. ............ 378/150 |
| 4,604,787 A | * | 8/1986 | Silvers, Jr. ............ 483/55 |
| 4,672,212 A | * | 6/1987 | Brahme .............. 250/505.1 |
| 4,754,147 A | * | 6/1988 | Maughan et al. ........ 250/505.1 |
| 4,965,726 A | * | 10/1990 | Heuscher et al. ......... 378/19 |
| 5,012,506 A | * | 4/1991 | Span et al. ............ 378/152 |
| 5,204,892 A | * | 4/1993 | Warden ............... 378/152 |
| 5,235,627 A | * | 8/1993 | Takagi ............... 378/151 |
| 5,237,599 A | * | 8/1993 | Gunji et al. ........... 378/148 |
| 5,332,908 A | * | 7/1994 | Weidlich ............. 250/492.1 |
| 5,396,534 A | * | 3/1995 | Thomas .............. 378/160 |
| 5,396,889 A | * | 3/1995 | Ueda et al. ............ 600/407 |
| 5,646,788 A | | 7/1997 | Bietry |
| 5,680,434 A | * | 10/1997 | Thelosen et al. ......... 378/150 |
| 5,748,703 A | * | 5/1998 | Cosman ............... 378/152 |
| 5,757,881 A | * | 5/1998 | Hughes ............... 378/65 |
| 5,847,388 A | | 12/1998 | Foote et al. |
| 5,945,684 A | * | 8/1999 | Lam et al. ............ 250/492.3 |
| 5,953,550 A | * | 9/1999 | Aoshima ............. 396/458 |
| 5,991,362 A | * | 11/1999 | Jones ................ 378/152 |

(Continued)

OTHER PUBLICATIONS

Coste-Maniere, E., "Robotic whole body stereotactic radiosurgery: clinical advantages of the CyberKnife® integrated system", The International Journal of Medical Robotics +Computer Assisted Surgery, 2005, www.roboticpublications.com, 14 pages.

(Continued)

*Primary Examiner* — Phillip A Johnston
*Assistant Examiner* — Michael J Logie
(74) *Attorney, Agent, or Firm* — Lowenstein Sandler PC

(57) ABSTRACT

An apparatus and method for coupling a fixed-aperture collimator to a variable-aperture collimator. The variable-aperture collimator may be an IRIS collimator having multiple leaves configured to open and close an aperture of the IRIS collimator within which the fixed-aperture collimator is retained.

30 Claims, 13 Drawing Sheets

U.S. PATENT DOCUMENTS

| | | | |
|---|---|---|---|
| 6,148,062 A * | 11/2000 | Romeas | 378/156 |
| 6,266,393 B1 * | 7/2001 | Ein-Gal | 378/152 |
| 6,459,769 B1 * | 10/2002 | Cosman | 378/147 |
| 6,714,627 B1 * | 3/2004 | Brown et al. | 378/152 |
| 6,822,252 B2 * | 11/2004 | Svatos et al. | 250/505.1 |
| 7,397,903 B2 * | 7/2008 | Yang | 378/152 |
| 7,508,918 B2 * | 3/2009 | Liu et al. | 378/152 |
| 7,783,007 B2 * | 8/2010 | Echner | 378/65 |
| 2001/0005409 A1 * | 6/2001 | Gohno et al. | 378/19 |
| 2004/0013237 A1 * | 1/2004 | Brown et al. | 378/147 |
| 2004/0066904 A1 * | 4/2004 | Eberhard et al. | 378/147 |
| 2004/0174949 A1 * | 9/2004 | Yamashita et al. | 378/65 |
| 2004/0184579 A1 * | 9/2004 | Mihara et al. | 378/65 |
| 2005/0197564 A1 * | 9/2005 | Dempsey | 600/411 |
| 2009/0074148 A1 * | 3/2009 | Echner | 378/152 |
| 2010/0054408 A1 | 3/2010 | Echner | |

OTHER PUBLICATIONS

International Search Report and Written Opinion, PCT/US08/004883 filed Apr. 15, 2008, mailed Aug. 1, 2008.

* cited by examiner

INTEGRATED VARIABLE-APERTURE COLLIMATOR AND FIXED-APERTURE COLLIMATOR

TECHNICAL FIELD

This invention relates to the field of radiation treatment and in particular, an apparatus and a method for coupling a fixed-aperture collimator to a variable-aperture collimator in a radiation treatment system.

BACKGROUND

Some of the clinical requirements of designing a radiosurgical treatment system include providing: a) a highly precise beam delivery to targets located throughout the body, b) a highly conformal dose distribution, c) the ability to irradiate both small and/or large complex-shaped lesions. To do this, the system uses a combination of beam positions whose relative beam weights, or dose contributions, have been scaled to volumetrically shape the dose accordingly. One or more collimators can be selected to give the beams the required shape to achieve the desired clinical result. Collimators are used in linear accelerators (LINACs) of radiation treatment systems, such as radiosurgery or radiotherapy systems. The collimators help to shape the beam of radiation emerging from the LINAC, and they can limit the maximum field size of the beam. The treatment head of the LINAC typically includes both a primary collimator and a secondary collimator.

Current radiation treatment surgery system such as the CYBERKNIFE® radiosurgery system, manufactured by Accuray™ Incorporated, USA, relies on a set of twelve circular, fixed-aperture secondary collimators to reduce the beam to the size required by the treatment planning algorithm. Because the apertures of these secondary collimators are of fixed-size, one fixed-aperture collimator individually does not provide flexibility of having an aperture of different sizes. The set of fixed-aperture secondary collimators are used to provide this flexibility; however, when a different size of aperture is to be used in the radiation treatment system, the fixed-aperture collimator needs to be changed. Currently changing of these collimators is accomplished manually by hand.

FIGS. 1 and 2 illustrate the conventional process of manually changing fixed-aperture collimators. FIG. 1 shows a locking nut 101 being removed by unscrewing the locking nut 101 and releasing the fixed-aperture collimator 102 from a collimator housing 103. Subsequently, the fixed-aperture collimator 102 may be replaced by another collimator by screwing the locking nut 101 to the collimator housing 103. In this implementation of changing fixed-aperture collimators with CYBERKNIFE® radiosurgery system, manufactured by Accuray™ Incorporated, USA, the locking nut 101 has to be rotated by hand to release the fixed-aperture collimator from off the end of a LINAC. FIG. 2 illustrates the fixed-aperture collimator 102 released from the collimator housing 103 during a manual process of changing the fixed-aperture collimator.

One conventional process for manually changing the collimators includes the following operations. First, the operator removes the locking nut 101 by unscrewing it from the collimator housing 103. Next, the operator, using his/her hand, supports the fixed-aperture collimator 102 from the bottom. Next, the operator releases a retaining pin to release the fixed-aperture collimator 102 from the collimator housing 103 to the operator's hand. Next, the operator selects a different fixed-aperture collimator and inserts the different fixed-aperture collimator into the collimator housing 103 until the retaining pin clicks. Lastly, the operator replaces the locking nut 101 and screws the locking nut 101 to the collimator housing 103. In this conventional process, the locking not 101 has to be turned multiple turns to be removed from the end of the LINAC.

Another conventional type of collimator, illustrated in FIG. 3, is an IRIS collimator 300, which includes a mechanism for varying the IRIS aperture 301 of the collimator 300 to adjust the beam width in radiosurgery and radiation therapy applications. The IRIS collimator 300 is typically used as secondary collimator. The IRIS collimator 300 includes multiple leaves 302 that are each driven linearly, which collectively closes and opens the IRIS aperture 301 of the collimator 300, varying the size of the IRIS aperture 301. Although, the IRIS collimator 300 is configured to provide flexibility in varying the size of the aperture 301 of the collimator, however, practical implementations of the IRIS collimator 300 suffer from having an aperture that is non-circular due to the mechanical limitations in the number of moving parts of the IRIS collimator 300.

DESCRIPTION OF THE DRAWINGS

The present invention is illustrated by way of example, and not by way of limitation, in the figures of the accompanying drawings.

DETAILED DESCRIPTION

Figure 1:
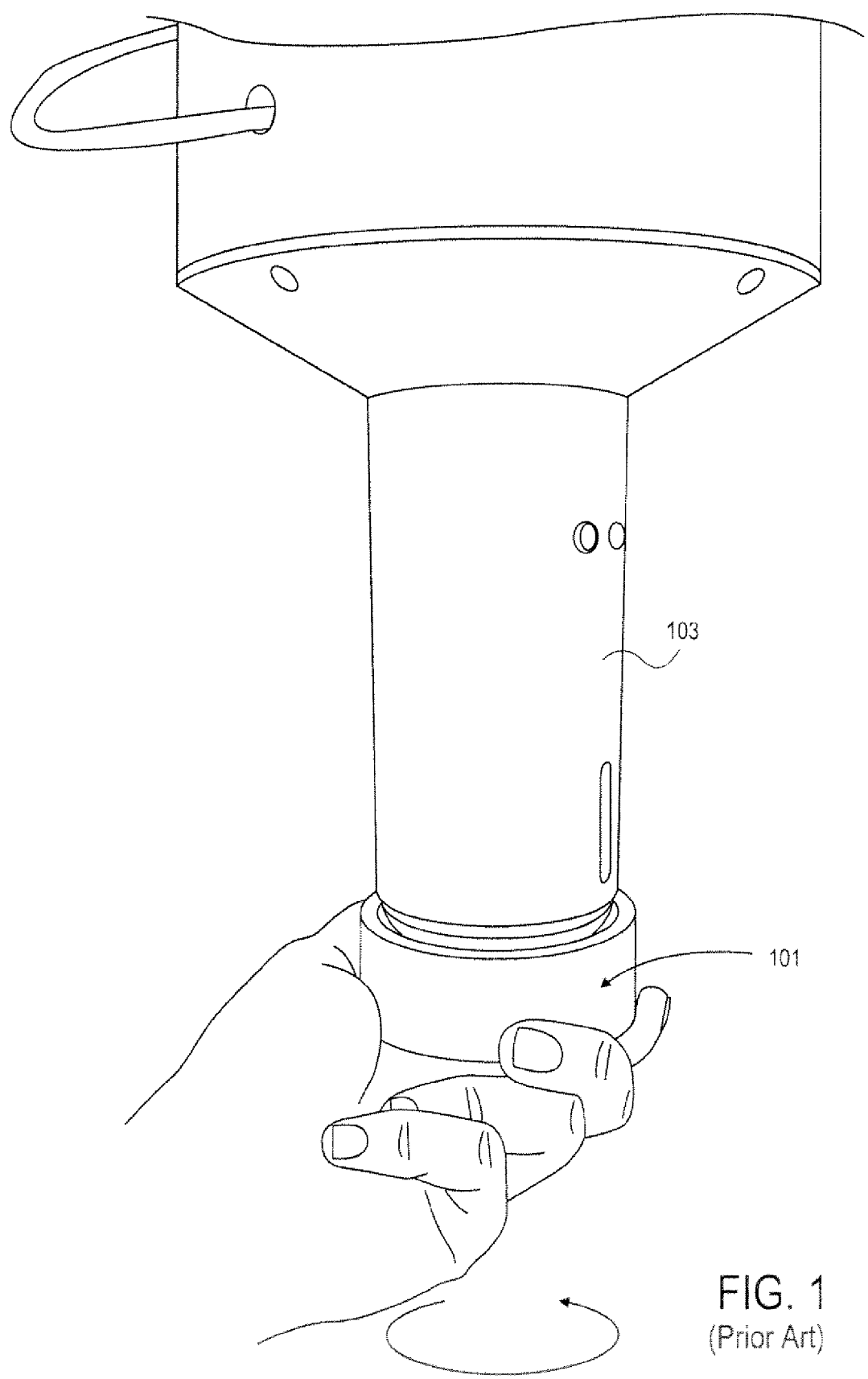
FIG. 1 illustrates a manual process of changing a fixed-aperture collimator.

Described herein are a method and an apparatus for coupling a fixed-aperture collimator to a variable-aperture collimator. The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

As described in greater detail below, the embodiments described herein include an integrated collimator for use in radiation treatment system. The integrated collimator may include a variable-aperture collimator and a fixed-aperture collimator coupled to the variable-aperture collimator. At least a portion of the outer-diameter surface of the fixed-aperture collimator is coupled to the inner-diameter surface of the variable-aperture collimator. The variable-aperture collimator may be a secondary collimator coupled to the end of the primary collimator at which the radiation beam exits the primary collimator. The LINAC may be a robot-based or a gantry-based LINAC. The robot-based LINAC may be coupled to a robot arm.

The variable-aperture collimator may be an IRIS collimator having multiple leaves configured to open and close an aperture of the IRIS collimator. In one embodiment, the IRIS collimator may be an IRIS collimator developed by Deutsche Krebsforschungszentrum (DKFZ), Hiedelberg, Germany. Alternatively, the IRIS collimator may be other types of IRIS collimators. The IRIS collimator may be a six-sided IRIS collimator having six leaves to open and close the aperture of the IRIS collimator. Alternatively, other numbers of leaves may be used in the IRIS collimator.

The integrated collimator may also include two variable-aperture collimators coupled to the end of the primary collimator at which the radiation beam exits the primary collimator. The two variable-aperture collimators and the fixed-aperture collimator may be a secondary collimator of the LINAC. A first portion of the outer-diameter surface of the fixed-aperture collimator is coupled to the inner-diameter surface of the first variable-aperture collimator and a second portion of the outer-diameter surface of the fixed-aperture collimator is coupled to the inner-diameter surface of the second variable-aperture collimator. The first and second variable-aperture collimators may each be an IRIS collimator having multiple leaves that are configured to open and close apertures of the respective collimators. The fixed-aperture collimator may have two sections, one section that couples to the first variable-aperture collimator and a second section that couples to the second variable-aperture collimator. The width of the first section, which is closer to the primary collimator, may be wider than the width of the second section, which is closer to the end of the LINAC at which the radiation beam exits the LINAC. Alternatively, the first section and second sections may have similar widths.

The embodiments described herein may allow a radiation treatment system to have both the flexibility of having an aperture of different sizes in the secondary collimator, and the possibility of using a fixed-aperture collimator having a circular aperture. The different sizes may be accomplished using the variable-aperture collimator with or without the use of the different fixed-aperture collimators.

The embodiments described herein may also be used to automatically change fixed-aperture collimators. These embodiments may rely on the radiation treatment robot (e.g., robotic arm coupled to a LINAC) to accomplish changing of the collimators, instead of relying on an operator to manual switch the fixed-aperture collimators as done conventionally.

Figure 4A:
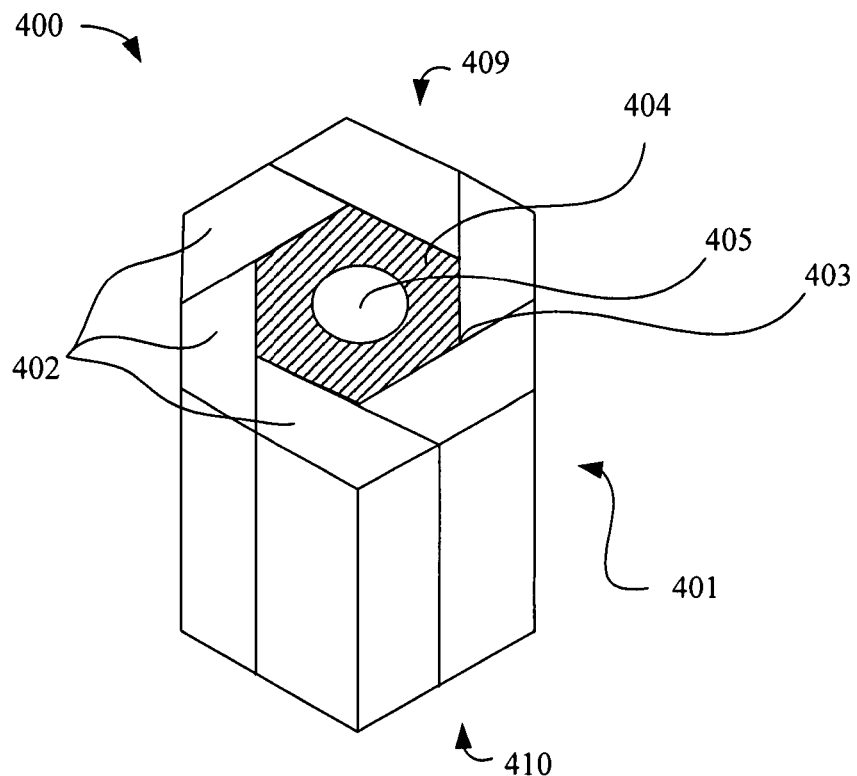
FIG. 4A illustrates a top view of one embodiment of an integrated collimator having a variable-aperture collimator and a fixed-aperture collimator.
Figure 4B:
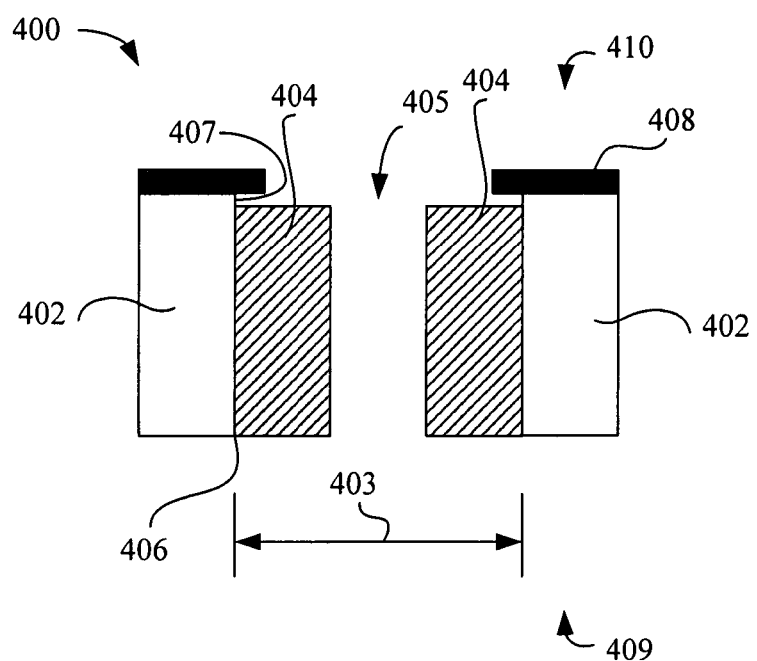
FIG. 4B illustrates a cross-sectional view of the integrated collimator of FIG. 4A.

FIGS. 4A and 4B illustrate a top view and a cross-sectional view of one embodiment of an integrated collimator 400 having a variable-aperture collimator 401 and a fixed-aperture collimator 404. The variable-aperture collimator 401 has six leaves 402 that are configured to open and close, varying the size of the aperture 403 of the variable-aperture collimator 401. When the fixed-aperture collimator 404 is coupled to the variable-aperture collimator 401, at least a portion of the outer-diameter surface 406 of the fixed-aperture collimator 404 is coupled to the inner-diameter surface 407 of the variable-aperture collimator 401. Alternatively, the variable-aperture collimator 401 may have more or less leaves than six.

In one embodiment, the integrated collimator 400 is a secondary collimator of a robot-based or a gantry-based LINAC, and is coupled to the end 409 of the primary collimator at which the radiation beam exits the primary collimator. In another embodiment, the integrated collimator 400 is a primary collimator of the LINAC and is coupled to radiation source of the LINAC. Alternatively, the integrated collimator 400 is one collimator of one or more collimators of LINAC that are used by the LINAC to help shape the beam of radiation emerging from the LINAC, and to help limit the maximum field size of the radiation beam.

In one embodiment, the variable-aperture collimator 401 is coupled to the end 409 of the LINAC at which the radiation beam exits the LINAC. The fixed-aperture collimator 404 is coupled to the variable-aperture collimator 401 by closing the aperture 403 of the variable-aperture collimator to retain the fixed-aperture collimator 404 within the variable-aperture collimator 401. In particular, with the aperture 403 opened, at least a portion of the fixed-aperture collimator 404 is disposed within the aperture 403. Once the fixed-aperture collimator 404 is disposed within the aperture 403, the aperture 403 is closed using the leaves 402 of the variable-aperture collimator 401. The outer-diameter surface 406 of the fixed-aperture collimator 404 is retained within the inner-diameter surface 407 of the variable-aperture collimator 401. In one embodiment, the fixed-aperture collimator 404 is positioned automatically in the aperture 403 of the variable-aperture collimator 401. This may include moving the variable-aperture collimator 401 using a robotic arm coupled to the variable-aperture collimator 401. Alternatively, the fixed-aperture collimator 404 may be positioned manually in the aperture 403 of the variable-aperture collimator 401.

In one embodiment, the variable-aperture collimator 401 of the integrated collimator 400 is an IRIS collimator 401 having six leaves 402 configured to open and close the aperture 403 of the IRIS collimator 401. The leaves 402 of the IRIS collimator 401 are driven by one or more drive mechanisms coupled to the leaves 402. The one or more drive mechanisms may be programmable drive mechanisms. Alternatively, the variable-aperture collimator 401 may be an IRIS collimator having more or less leaves than six.

In one embodiment, the integrated collimator 400 includes one or more retention mechanisms 408 coupled to the variable-aperture collimator 401 to retain the fixed-aperture collimator 404 within the variable-aperture collimator 401. For example, the one or more retention mechanisms 408 may be used to prevent the fixed-aperture collimator 404 that is disposed within the variable-aperture collimator 401 from going beyond a certain point in the collimator housing. Alternatively, the retention mechanisms 408 may be used to secure and retain the fixed-aperture collimator 404 in a particular position within the variable-aperture collimator 401. The retention mechanism 408 may be one or more stoppers coupled to the end 410 of the variable-aperture collimator 401 closest to the radiation source (as illustrated in FIG. 4B). In another embodiment, the retention mechanism 408 is a locking nut (e.g., similar to the locking nut 101 of FIG. 1) coupled to the end 409 of the variable-aperture collimator 401 at which the radiation beam exits the variable-aperture collimator 401 to retain the fixed-aperture collimator 404 within the variable-aperture collimator 401, and/or to prevent the fixed-aperture collimator 404 from falling out of the variable-aperture collimator 401. Alternatively, other types of retention mechanisms known by those of ordinary skill in the art may be used.

Figure 5A:
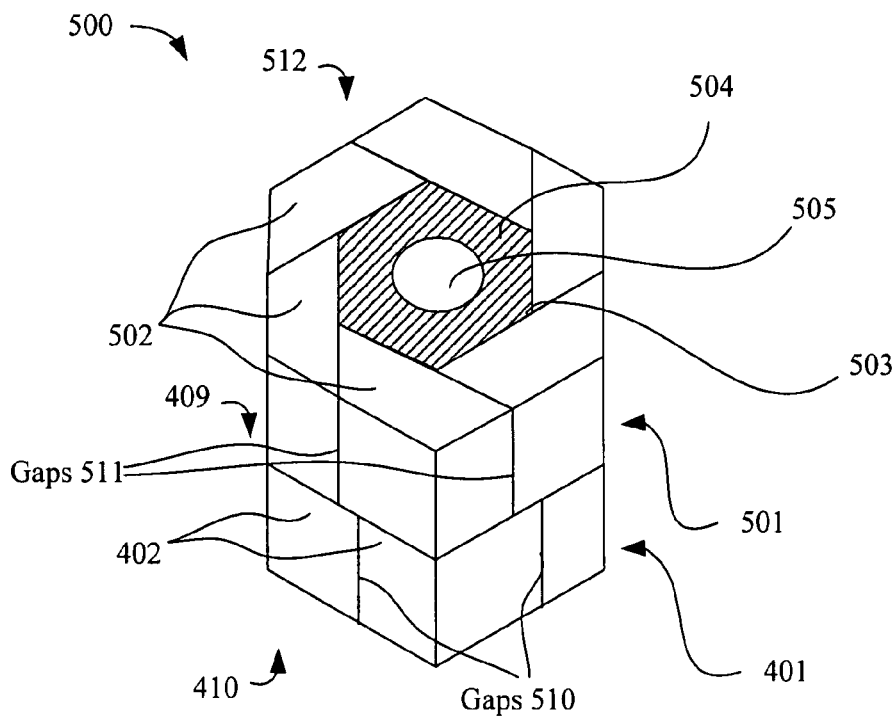
FIG. 5A illustrates a top view of one embodiment of an integrated collimator having two variable-aperture collimators and a fixed-aperture collimator.
Figure 5B:
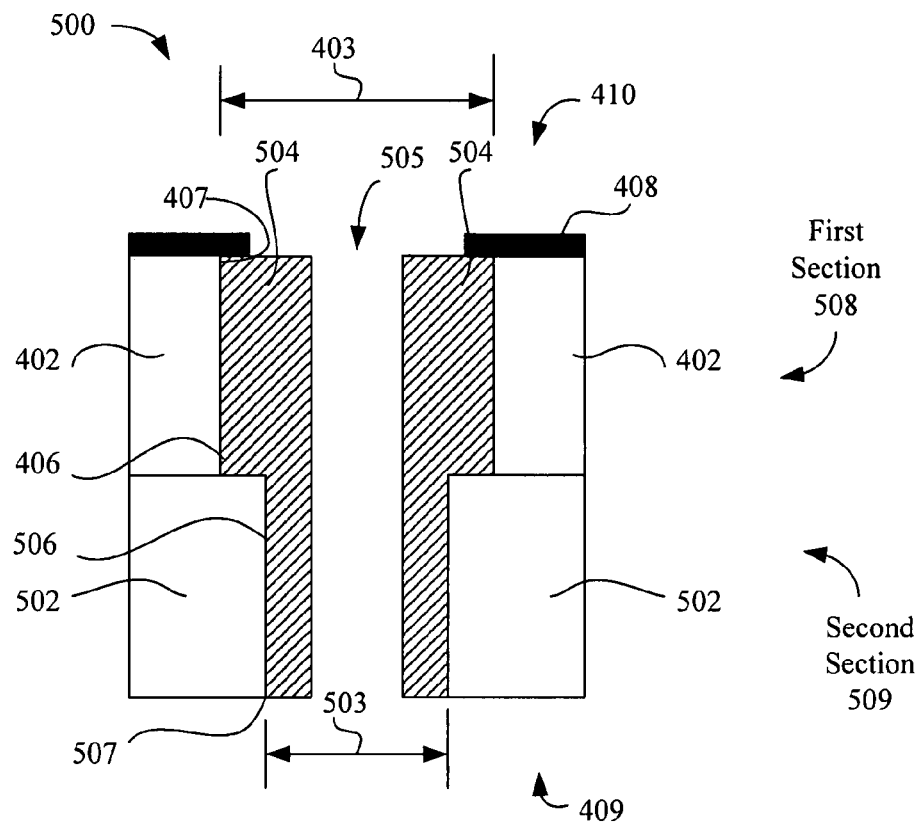
FIG. 5B illustrates a cross-sectional view of the integrated collimator of FIG. 5A.

FIGS. 5A and 5B illustrate a top view and a cross-sectional view of one embodiment of an integrated collimator 500 having two variable-aperture collimators 401 and 501 and a fixed-aperture collimator 504. The variable-aperture collimator 401 is similar to the variable-aperture collimator 401 described with respect to FIGS. 4A and 4B. The variable-aperture collimator 501 is coupled to the end 409 of the variable-aperture collimator 401 at which the radiation beam exits the variable-aperture collimator 401. The variable-aperture collimator 501 also has six leaves 502 that are configured to open and close, varying the size of the aperture 503 of the variable-aperture collimator 501. Alternatively, the variable-aperture collimator 501 may have more or less leaves than six. When the fixed-aperture collimator 504 is coupled to the variable-aperture collimators 401 and 501, at least a first portion 406 of the outer-diameter surface of the fixed-aperture collimator 504 is coupled to the inner-diameter surface 407 of the variable-aperture collimator 401, and at least a second portion 506 of the outer-diameter surface of the fixed-aperture collimator 504 is coupled to the inner-diameter surface 507 of the variable-aperture collimator 501.

In one embodiment, the integrated collimator 500 is a secondary collimator of a robot-based or a gantry-based LINAC, and is coupled to the end of the primary collimator at which the radiation beam exits the primary collimator. In another embodiment, the integrated collimator 500 is a primary collimator of the LINAC and is coupled to radiation source of the LINAC. Alternatively, the integrated collimator 500 is one collimator of one or more collimators of LINAC that are used by the LINAC to help shape the beam of radiation emerging from the LINAC, and to help limit the maximum field size of the radiation beam.

In one embodiment, the variable-aperture collimator 401 is coupled to the end of the LINAC at which the radiation beam exits the LINAC, and the variable-aperture collimator 501 is coupled to the to the end 409 of the variable-aperture collimator 401 at which the radiation beam exits the variable-aperture collimator 401. The variable-aperture collimators 401 and 501 are configured to retain the fixed-aperture collimator 504 within the apertures 403 and 503 of the variable-aperture collimators 401 and 501. The fixed-aperture collimator 504 is coupled to the variable-aperture collimators 401 and 501 by closing the apertures 403 and 503 of the variable-aperture collimators to retain the fixed-aperture collimator 504 within the variable-aperture collimators 401 and 501. In particular, with the apertures 403 and 503 opened, at least a first portion 406 of the fixed-aperture collimator 504 is disposed within the aperture 403, and at least a second portion 506 of the fixed-aperture collimator 504 is disposed within the aperture 503. Once the fixed-aperture collimator 504 is disposed within the apertures 403 and 503, the apertures 403 and 503 are closed using the leaves 402 and 502 of the variable-aperture collimators 401 and 501, respectively. A first section 508 of the fixed-aperture collimator 504 is retained within the variable-aperture collimator 401, and a second section 509 of the fixed-aperture collimator 504 is retained within the variable-aperture collimator 501. In particular, the first portion 406 of the outer-diameter surface of the fixed-aperture collimator 504 is retained by the inner-diameter surface 407 of the variable-aperture collimator 401, and the second portion 506 of the outer-diameter surface of the fixed-aperture collimator 504 is retained by the inner-diameter surface 507 of the variable-aperture collimator 501. In one embodiment, the first section 508 is wider than the second section 509 of the fixed-aperture collimator 504. Alternatively, the first section 507 and the second section 509 may have similar widths.

In one embodiment, the fixed-aperture collimator 504 is positioned automatically in the apertures 403 and 503 of the variable-aperture collimators 401 and 501. This may include moving the variable-aperture collimators 401 and 501 using a robotic arm coupled to the variable-aperture collimators 401 and 501. Alternatively, the fixed-aperture collimator 504 may be positioned manually in the apertures 403 and 503 of the variable-aperture collimators 401 and 501.

In one embodiment, the variable-aperture collimators 401 and 501 of the integrated collimator 500 are IRIS collimators 401 and 501 having six leaves 402 and 502 configured to open and close the apertures 403 and 503 of the IRIS collimators 401 and 501. The leaves 402 and 502 of the IRIS collimators 401 and 501 are driven by one or more drive mechanisms coupled to the leaves 402 and 502. The one or more drive mechanisms may be programmable drive mechanisms. In one embodiment, a first programmable drive mechanism is coupled to the leaves 402 of the variable-aperture collimator 401, and a second programmable drive mechanism is coupled to the leaves 502 of the variable-aperture collimator 501. The first and second programmable drive mechanisms may be configured to drive the leaves 402 and 502 independently. The first programmable drive mechanism is configured to drive the leaves 402, opening and closing the aperture 403 of the variable-aperture collimator 401. The second programmable drive mechanism is configured to drive the leaves 502, opening and closing the aperture 503 of the variable-aperture collimator 501. The first and second programmable drive mechanisms may be configured to drive the leaves 402 and 502 substantially sequentially, such as, for example, opening the leaves 402, then opening the leaves 502, and closing the leaves 502, then closing the leaves 402. Alternatively, the first and second drive mechanisms may be configured to drive the leaves 402 and 502 substantially simultaneously, such as, for example, opening the leaves 402 and 502 substantially simultaneously, and closing the leaves 402 and 502 substantially simultaneously. Alternatively, the first and second programmable drive mechanisms may be configured to synchronize the movement of the leaves 402 and 502 in other patterns.

Although the IRIS collimators 401 and 501 of FIGS. 5A and 5B are six-sided IRIS collimators, alternatively, the variable-aperture collimators 401 and 501 may be IRIS collimators having more or less leaves than six.

In one embodiment, the leaves 402 and 502 of the variable-aperture collimators 401 and 501 are disposed such that the gaps 510 between the leaves 402 are not aligned with the gaps 511 between leaves 502. By having the gaps 510 and 511 not be aligned, the variable-aperture collimators 401 and 501 may prevent or reduce the radiation leakage from the radiation beam received from the radiation source or from the primary collimator that is coupled to the integrated collimator 500. For example, if the gaps 510 and 511 of the variable-aperture collimators 401 and 501 were aligned, the radiation beam received from the radiation source or primary collimator would be allowed through the gaps 510 and 511.

In one embodiment, the integrated collimator 500 includes one or more retention mechanisms 408 coupled to the variable-aperture collimator 401 to retain the fixed-aperture collimator 504 within the variable-aperture collimators 401 and 501. For example, the one or more retention mechanisms 408 may be used to prevent the fixed-aperture collimator 504 that is disposed within the variable-aperture collimators 401 and 501 from going beyond a certain point in the collimator housing. Alternatively, the retention mechanisms 408 may be used to secure and retain the fixed-aperture collimator 504 in a particular position within the variable-aperture collimators 401 and 501. The retention mechanism 408 may be one or more stoppers coupled to the end 410 of the variable-aperture collimator 401 that is closest to the radiation source (as illustrated in FIG. 5B). In another embodiment, the retention mechanism 408 is a locking nut (e.g., similar to the locking nut 101 of FIG. 1) coupled to the end 512 of the variable-aperture collimator 501 at which the radiation beam exits the variable-aperture collimator 501 to retain the fixed-aperture collimator 504 within the variable-aperture collimators 401 and 501, and/or to prevent the fixed-aperture collimator 504 from falling out of the variable-aperture collimators 401 and 501. Alternatively, other types of retention mechanisms known by those of ordinary skill in the art may be used.

Figure 5C:
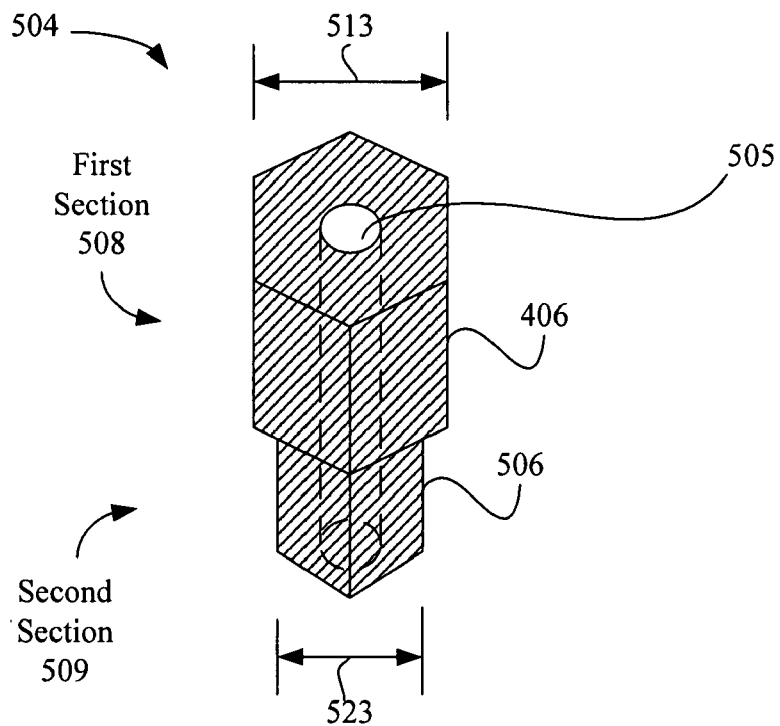
FIG. 5C illustrates a top view of one embodiment of a fixed-aperture collimator having two sections of different widths and similar shapes.

FIG. 5C illustrates a top view of one embodiment of a fixed-aperture collimator 504 having two sections 508 and 509 of different widths and similar shapes. In this embodiment, the first section 508 of the fixed-aperture collimator 504 has a hexagon shape on the outer-diameter surface 406. The first section 508 of the fixed-aperture collimator 504 has a width 513. The width 513 is approximately equal to the width of the aperture 403 of the variable-aperture collimator 401 when the aperture 403 is closed to retain the fixed-aperture collimator 504. The second section 509 of the fixed-aperture collimator 504 also has a hexagon shape on the outer-diameter surface 506. The second section 509 of the fixed-aperture collimator 504 has a width 523. The width 523 is approximately equal to the width of the aperture 503 of the variable-aperture collimator 501 when the aperture 503 is closed to retain the fixed-aperture collimator 504. Both the inner-diameter surfaces of the apertures 403 and 503 of the fixed-aperture collimator 504 are circular about the longitudinal axis. Alternatively, other shapes may be used, such as ovals, squares, rectangles, or the like. In this embodiment, the width 513 is greater than the width 514. Alternatively, the widths of the two sections are similar in widths, as illustrated in FIG. 5D.

Figure 5D:
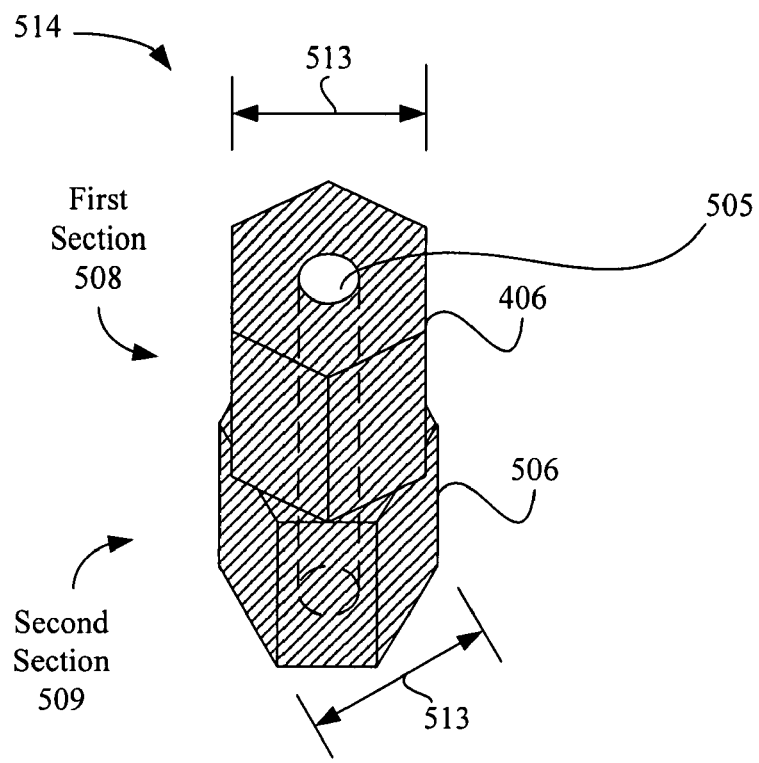
FIG. 5D illustrates a top view of one embodiment of a fixed-aperture collimator having two sections of similar widths and similar shapes.

FIG. 5D illustrates a top view of one embodiment of a fixed-aperture collimator 514 having two sections 508 and 509 of similar widths and similar shapes. In this embodiment, the first section 508 of the fixed-aperture collimator 514 has a hexagon shape on the outer-diameter surface 406 and a width 513. The width 513 is approximately equal to the width of the aperture 403 of the variable-aperture collimator 401 when the aperture 403 is closed to retain the fixed-aperture collimator 514. The second section 509 of the fixed-aperture collimator 504 also has a hexagon shape on the outer-diameter surface 506 and the same width 513. The width 513 is approximately equal to the width of the aperture 503 of the variable-aperture collimator 501 when the aperture 503 is closed to retain the fixed-aperture collimator 514. In this embodiment, the outer-diameter surface 506 and 406 are not aligned. By not aligning the outer-diameter surfaces 506 and 406 of the fixed-aperture collimator 514, when the variable-aperture collimators 401 and 501 have been closed on the fixed-aperture collimator 514, the gaps between the leaves of the variable-aperture collimators 401 and 501 are not aligned, such as gaps 510 and 511 between the leaves 402 and leaves 502 of the variable-aperture collimators 401 and 501, respectively. Both the inner-diameter surfaces of the aperture 505 of the fixed-aperture collimator 504 are circular about the longitudinal axis. Alternatively, other shapes may be used, such as ovals (such as illustrated in FIG. 5E), squares, rectangles, or the like.

Figure 5E:
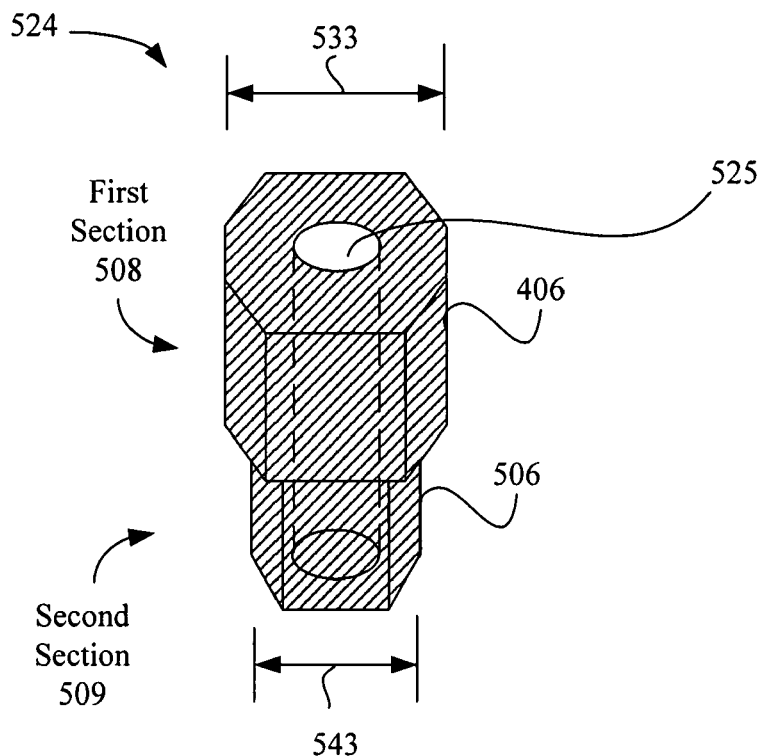
FIG. 5E illustrates a top view of another embodiment of a fixed-aperture collimator having two sections of different widths and similar shapes.

FIG. 5E illustrates a top view of another embodiment of a fixed-aperture collimator 524 having two sections 508 and 509 of different widths and similar shapes shapes. In this embodiment, the first section 508 of the fixed-aperture collimator 504 has an octagon shape on the outer-diameter surface 406 and a width 533. The width 533 is approximately equal to the width of the aperture 403 of the variable-aperture collimator 401 when the aperture 403 is closed to retain the fixed-aperture collimator 524. The second section 509 of the fixed-aperture collimator 524 also has an octagon shape on the outer-diameter surface 506 and a width 543. The width 543 is approximately equal to the width of the aperture 503 of the variable-aperture collimator 501 when the aperture 503 is closed to retain the fixed-aperture collimator 524. In this embodiment, the width 533 is greater than the width 543. Alternatively, the widths of the two sections are similar in widths, as illustrated in FIG. 5D. Both the inner-diameter surfaces of the aperture 525 of the fixed-aperture collimator 504 have an oval shape about the longitudinal axis. Alternatively, other shapes may be used, such as circles, squares, rectangles, or the like.

Figure 5F:
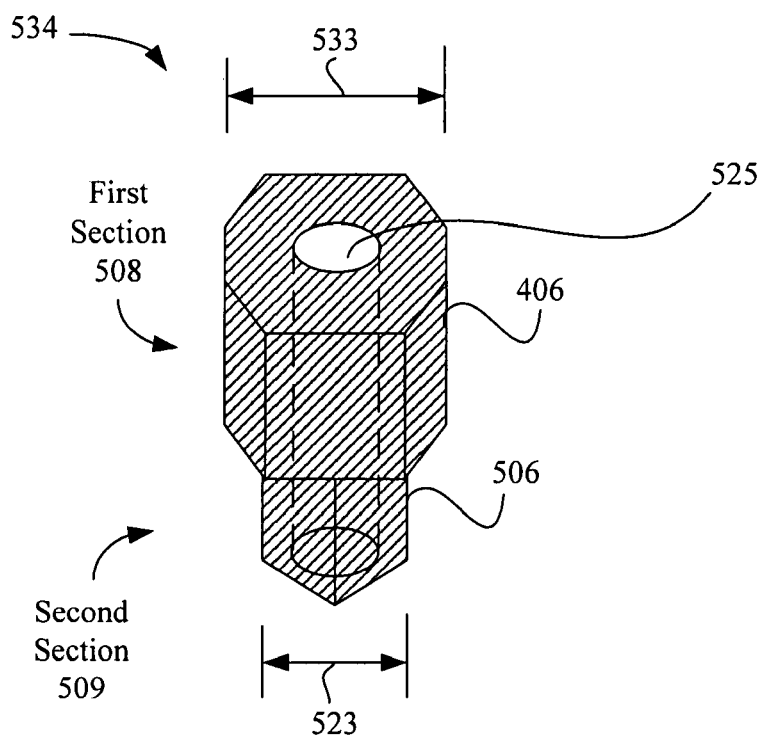
FIG. 5F illustrates a top view of one embodiment of a fixed-aperture collimator having two sections of different widths and dissimilar shapes.

Although the embodiments of FIGS. 5C, 5D, and 5E have fixed-aperture collimators with similar shapes for the two sections 508 and 509, alternatively, the two sections 508 and 509 may have dissimilar shapes, as illustrated in FIG. 5F.

FIG. 5F illustrates a top view of one embodiment of a fixed-aperture collimator 534 having two sections 508 and 509 of different widths and dissimilar shapes. In this embodiment, the first section 508 of the fixed-aperture collimator 534 has an octagon shape on the outer-diameter surface 406 and a width 533, similar to the first section 508 of FIG. 5E. The width 533 is approximately equal to the width of the aperture 403 of the variable-aperture collimator 401 when the aperture 403 is closed to retain the fixed-aperture collimator 534. The second section 509 of the fixed-aperture collimator 524 also has a hexagon shape on the outer-diameter surface 506 and a width 523, similar to the second section 509 of FIG. 5C. The width 523 is approximately equal to the width of the aperture 503 of the variable-aperture collimator 501 when the aperture 503 is closed to retain the fixed-aperture collimator 534. In this embodiment, the width 533 is greater than the width 523. Alternatively, the widths of the two sections are similar in widths, as illustrated in FIG. 5D. Both the inner-diameter surfaces of the aperture 525 of the fixed-aperture collimator 504 have an oval shape about the longitudinal axis. Alternatively, other shapes may be used, such as circles, squares, rectangles, or the like.

Although the apertures 405 and 505 (e.g., inner-diameter surfaces) of the fixed-aperture collimator 404 and 504 have been illustrated as having circular apertures 405 and 505 about a longitudinal axis of the fixed-aperture collimators 404 and 504, the apertures 405 and 505 have different shapes, such as ovals (such as aperture 525 of FIGS. 5E and 5F), rectangles, squares, or the like. Similarly, although the outer-diameter surfaces 406 and 506 of the fixed-aperture collimators 404 and 504 have been illustrated as having hexagonal or octagonal shape about a longitudinal axis of the fixed-aperture collimators 404 and 504, the outer-diameter surfaces 406 and 506 may have different shapes, such as square, rectangle, pentagon, or the like. The outer-diameter surfaces 406 or 506 of the fixed-aperture collimator 404 may have similar or dissimilar number of sides as the variable-aperture collimator 401 or 501. Also, the outer-diameter surfaces 406 and 506 may be different shapes, for example, the outer-diameter surface of the first section is a hexagon, and the outer-diameter surface of the second section is a square or rectangle.

Figure 6:
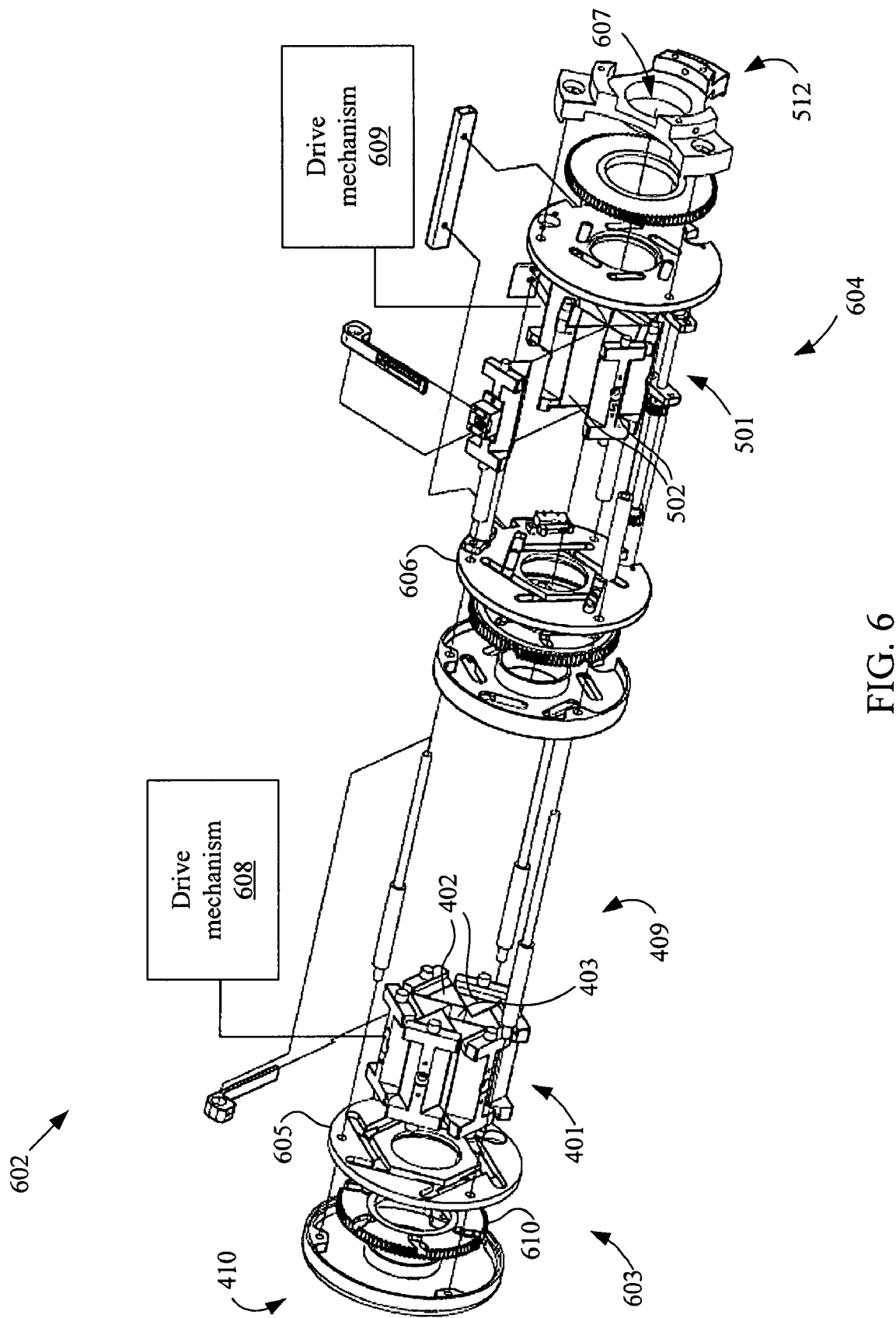
FIG. 6 illustrates a perspective view of another embodiment of an integrated collimator having two variable-aperture collimators for retaining a fixed-aperture collimator.

FIG. 6 illustrates a perspective view of another embodiment of an integrated, secondary collimator 602 having two variable-aperture collimators for retaining a fixed-aperture collimator. The integrated, secondary collimator 602 includes variable-aperture collimator 401 having multiple leaves 402, and variable-aperture collimator 501 having multiple leaves 502. The leaves 402 and leaves 502 are driven by drive mechanisms 608 and 609, to open and close apertures 403 and 503, respectively. In one embodiment, the drive mechanisms 608 and 609 are programmable drive mechanisms. In another embodiment, one drive mechanism may be used to drive the leaves 402 and leaves 502 to open and close apertures 403 and 503.

In this embodiment, the variable-aperture collimator 401 is disposed in a collimator housing 603, and the variable-aperture collimator 501 is disposed in a collimator housing 604. The collimator housing 603 is coupled to the collimator housing 604. In another embodiment, the collimator housings 603 and 604 are one integrated collimator housing.

The collimator housing 603 includes plate 605, and the collimator housing 604 includes plate 606. The plates 605 and 606 each include tracks within which each of the leaves 402 and 502 are disposed. The tracks are linear and allow the leaves 402 and 502 to be driven linearly back and forth along the tracks. Each of the leaves 402 and 502 are individually driven linearly by the drive mechanism 608 and 609, which collectively opens the apertures 403 and 503 of the variable-aperture collimators 401 and 501, respectively. The leaves 402 and 502 are opened and closed to retain a fixed-aperture collimator (not illustrated in FIG. 6) within the apertures 403 and 503 of the secondary, integrated collimator 602. The fixed-aperture collimator is positioned within the apertures 403 and 503 of the opened leaves 402 and 502. Once the fixed-aperture collimator is positioned within the apertures 403 and 503, the leaves 402 and 502 are driven closed to retain the fixed-aperture collimator within the secondary, integrated collimator 602. The fixed-aperture collimator is positioned through apertures 607 of the various components of the collimator housings 603 and 604 from the end 512 at which the radiation exits the collimator housings 603 and 604 of the LINAC. The collimator housings 603 and 604 include other mechanical components to support the variable-aperture collimators 401 and 501 within the collimator housings 603 and 604.

In one embodiment, the integrated, secondary collimator 602 includes one or more retention mechanisms to retain the fixed-aperture collimator (e.g., 404, 504, 514, 524, or 534) within the secondary collimator 602 in addition to the variable-aperture collimators 401 and 501. In one embodiment, the integrated, secondary collimator 602 includes stopper coupled to the end 410 of the variable-aperture collimator 401 that is closest to the radiation source. In another embodiment, the integrated, secondary collimator 602 includes a rotary stopper plate 610. The rotary stopper plate 610 is a rotary plate having slots. When the plate 610 rotates, the slots drag the pins of the leaves of the variable-aperture collimator 401 along a straight line, opening and closing the leaves of the variable-aperture collimator 401. In another embodiment, the integrated, secondary collimator 602 includes additional retention mechanisms, such as a locking nut (e.g., similar to the locking nut 101 of FIG. 1) that is screwed onto the end 512 of the variable-aperture collimator 501 at which the radiation beam exits the variable-aperture collimator 501. Alternatively, other retention mechanisms may be used to retain the fixed-aperture collimator within the integrated, secondary collimator 602 in addition to the leaves 402 and 502 of the variable-aperture collimators 401 and 501. The variable aperture collimators 401 and 501 in this embodiment operate as follows. The variable aperture collimator shown in this embodiment has six sides, although other configurations using 8, 12, or 16 are possible. In the illustrated embodiment, each of the 6 leaves of the collimator 401 (or 501) has a small cylindrical stub which fits into one of the 6 linear slots in the fixed disk 605, as well as into the curved cam shaft in the rotary stopper disk 610. When the rotary stopper plate 610 rotates, the stubs of the leaves of the collimator 401, move along the corresponding linear slots in the fixed disk 605, thereby opening or closing the aperture formed by the leaves of the collimator.

In this embodiment, the integrated collimator 602 is a secondary collimator. The integrated, secondary collimator 602 is coupled to the end of the primary collimator at which the radiation beam exits the primary collimator. In another embodiment, the integrated collimator 602 is a primary collimator and is coupled to a radiation source of the LINAC. Alternatively, the integrated collimator 602 may be used in other configurations know to those of ordinary skill in the art.

Figure 7:
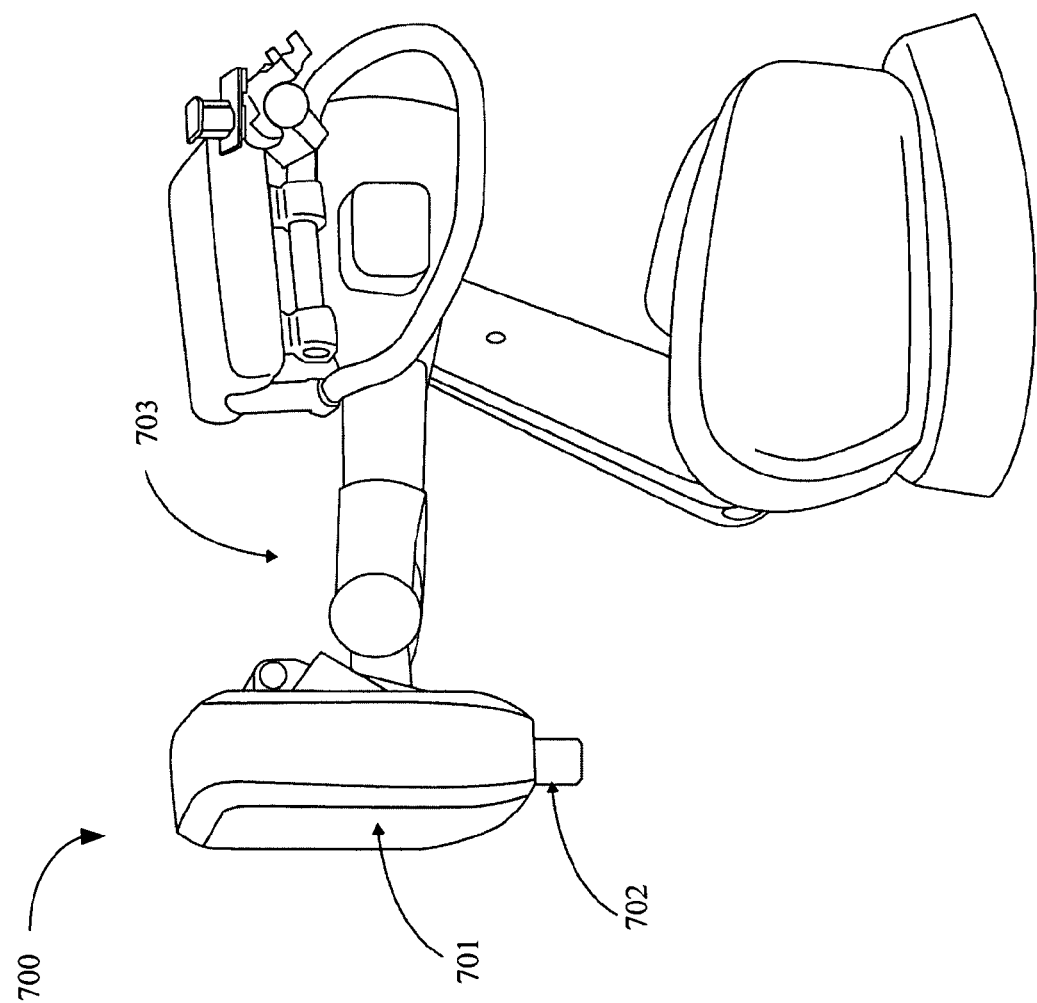
FIG. 7 illustrates one embodiment of a LINAC of a radiation treatment system, having an integrated collimator, coupled to a robotic arm.

FIG. 7 illustrates one embodiment of a LINAC 701 of a radiation treatment system 700, having an integrated collimator 702, coupled to a robotic arm 703. The radiation treatment system 700 includes the LINAC 701 coupled to the robotic arm 703. The robotic arm 703 is configured to move the LINAC 701 in multiple degrees of freedom, such as six degrees of freedom. The LINAC 701 includes a primary collimator (which is not illustrated) within the LINAC housing, and the integrated, secondary collimator 702, which is coupled to the end of the primary collimator at which the radiation beam exits the primary collimator. In one embodiment, the integrated, secondary collimator 702 includes one variable-aperture collimator 401 and the fixed-aperture collimator 404, as described with respect to FIGS. 4A and 4B. Alternatively, the integrated, secondary collimator 702 may include two variable-aperture collimators 401 and 501 and the fixed-aperture collimator 504, as described with respect to FIGS. 5A and 5B.

Although, the integrated collimator 702 of FIG. 7 is illustrated as being on robot-based LINAC, the integrated collimator 702 may be coupled to gantry-based LINAC.

Figure 8:
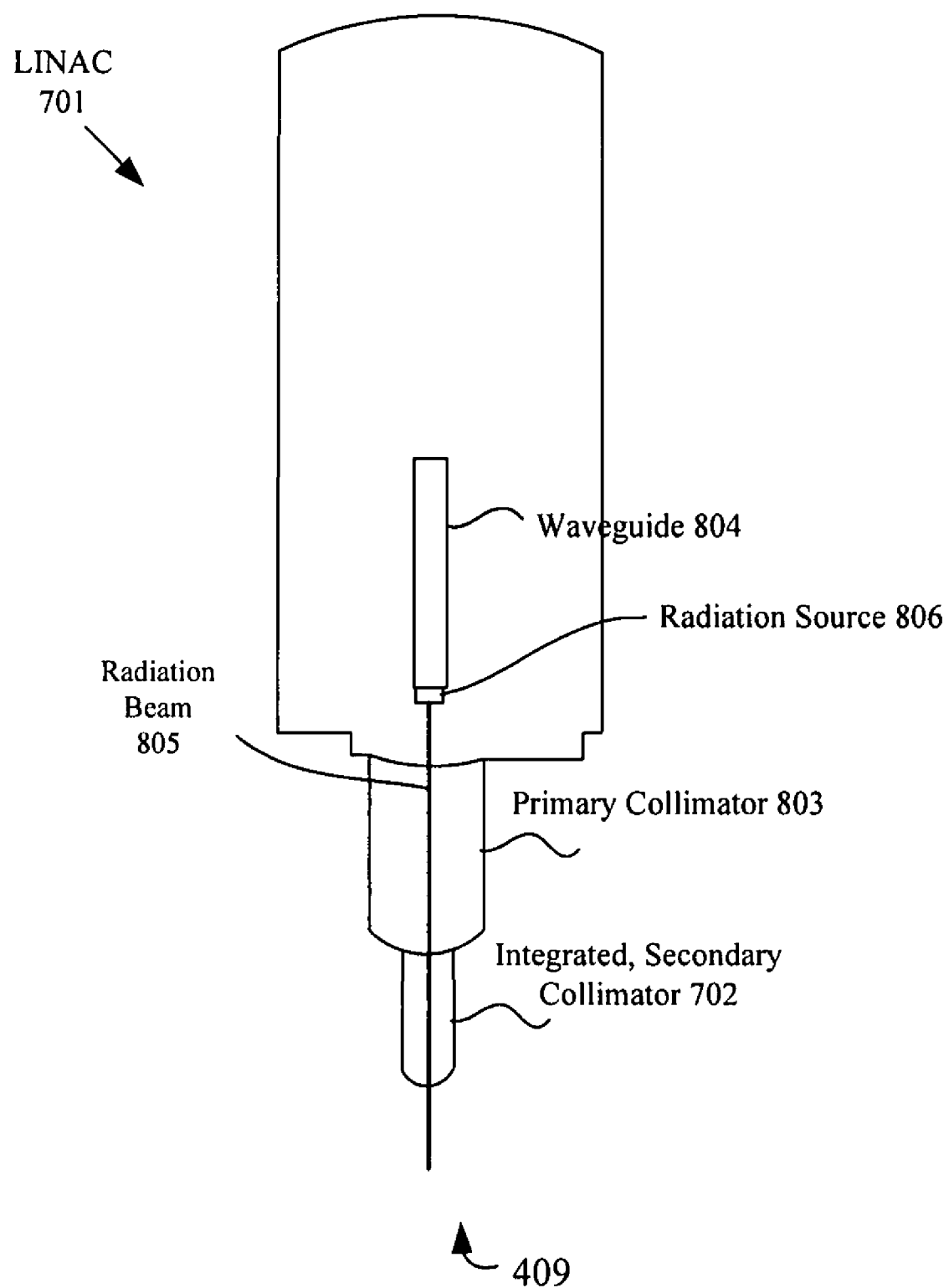
FIG. 8 illustrates one embodiment of a LINAC of the radiation treatment system of FIG. 7 having an integrated collimator.

FIG. 8 illustrates one embodiment of the LINAC 701 of the radiation treatment system 700 of FIG. 7 having the integrated, secondary collimator 702. The LINAC 701 includes radiation source 806, waveguide 804, primary collimator 803, and the integrated collimator 702. In LINAC 701, electrons from an electron gun at a negative potential are accelerated to the target (e.g., radiation source), which is held at a positive potential relative to the electron gun (e.g., at a system ground potential). The electrons are accelerated through a waveguide accelerator structure 804 as an electron beam that strikes an x-ray target (e.g., radiation source 806) to generate x-rays (e.g., radiation beam 805). The radiation beam 805 is directed towards the primary collimator 803 and the integrated, secondary collimator 702. From the integrated, secondary collimator 702, the radiation beam 805 is directed towards a target region, such as a target located within a body of a patient on a treatment couch. Additional details regarding the LINAC 701 are known to those of ordinary skill in the art and have not been illustrated or described so as to not obscure the embodiments described herein. The embodiments described herein are not limited to robotic-based radiation treatment system, but may also include other radiation treatment systems, such as gantry-based radiation treatment systems.

In one embodiment, the integrated, secondary collimator 702 includes one variable-aperture collimator 401 and the fixed-aperture collimator 404, as described with respect to FIGS. 4A and 4B. Alternatively, the integrated, secondary collimator 702 may include two variable-aperture collimators 401 and 501 and the fixed-aperture collimator 504, as described with respect to FIGS. 5A and 5B.

Figure 9A:
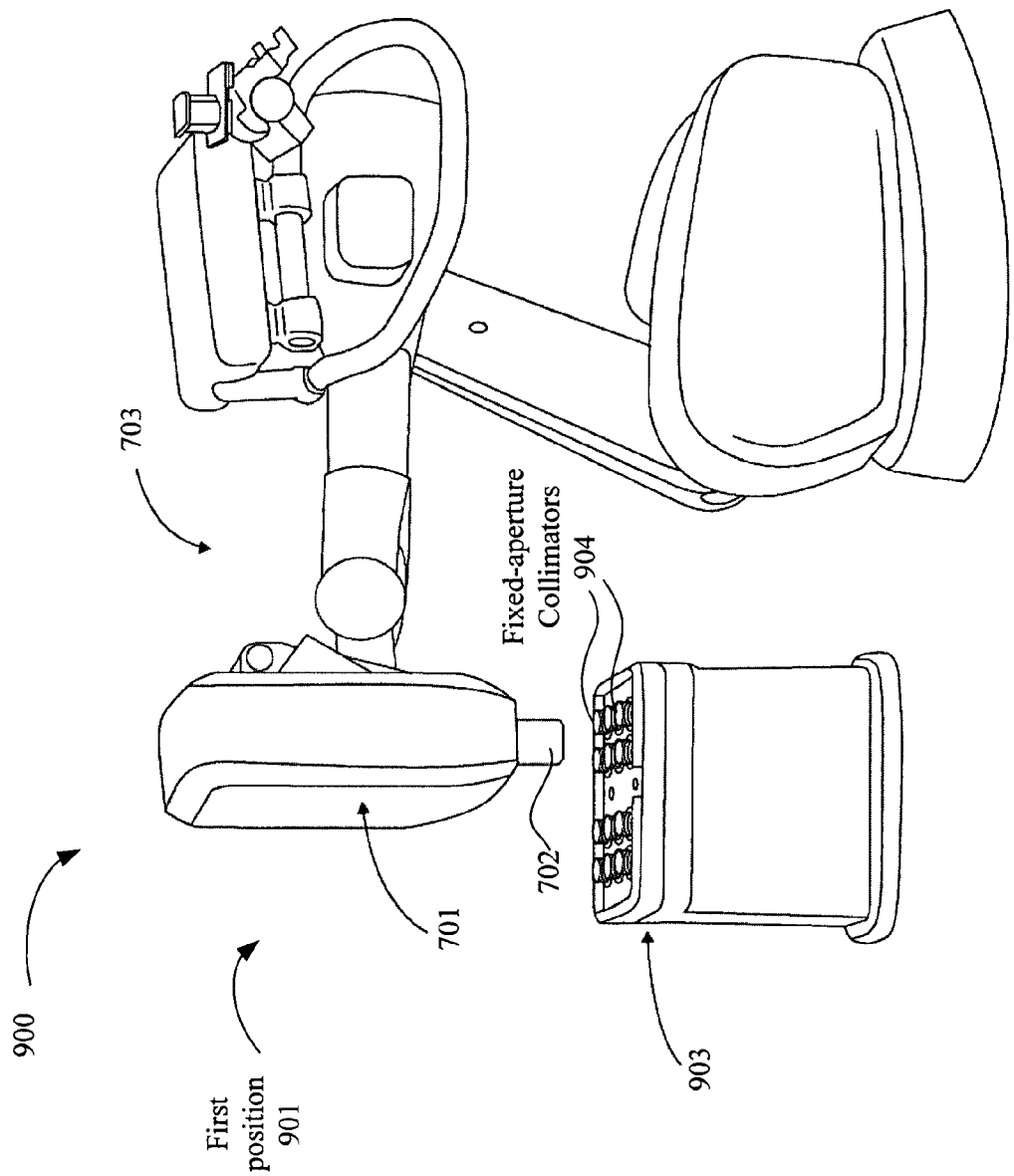
FIG. 9A illustrates one embodiment of a first position of a radiation treatment system for automatically changing fixed-aperture collimators using an integrated collimator.
Figure 9B:
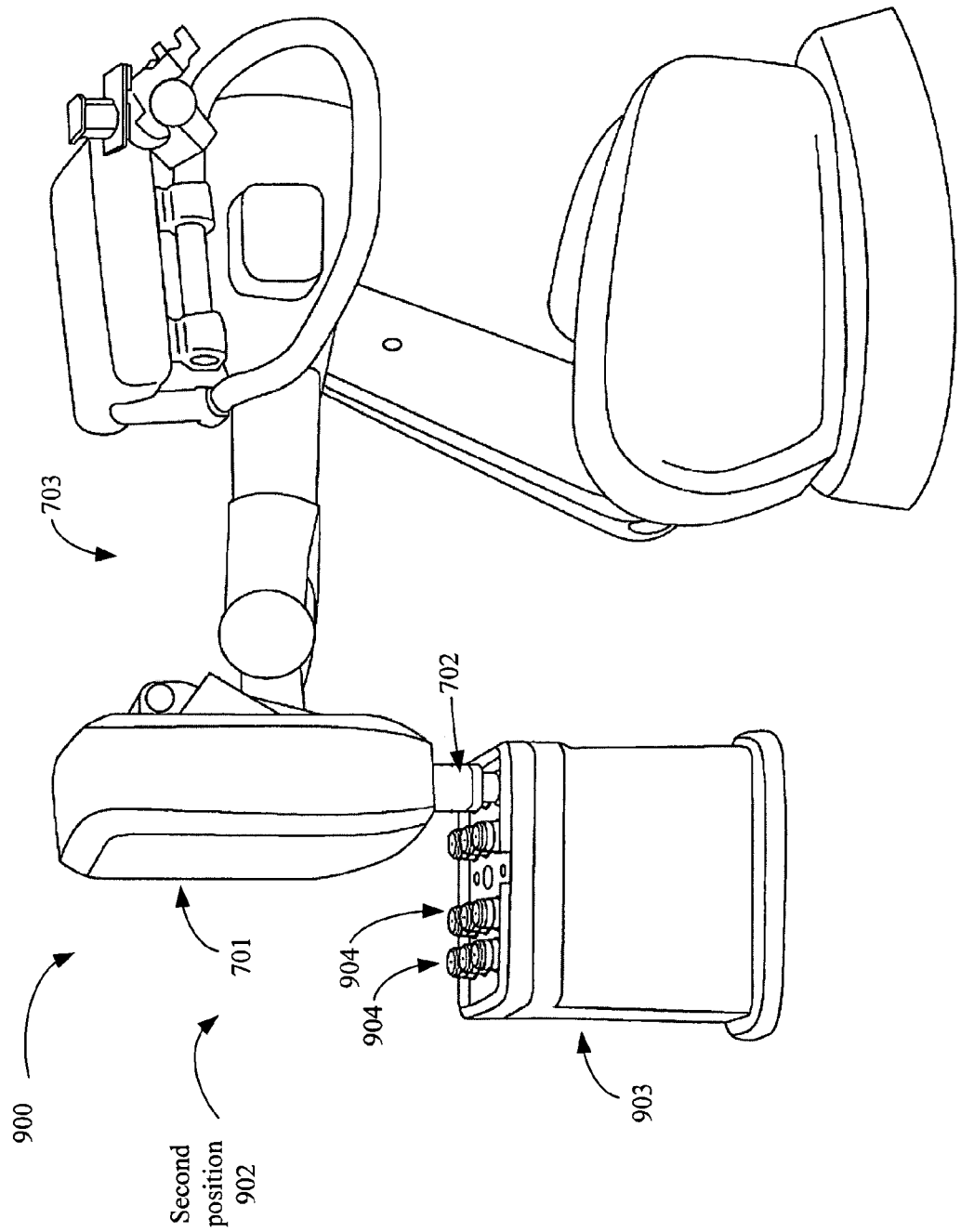
FIG. 9B illustrates a second position of the radiation treatment system of FIG. 9A for automatically changing fixed-aperture collimators using the integrated collimator.

FIGS. 9A and 9B illustrate one embodiment of a radiation treatment system 900 for automatically changing fixed-aperture collimators 904 using an integrated collimator 702. FIG. 9A illustrates a first position 901 of the radiation treatment system 900 and FIG. 9B illustrates a second position 902 of the radiation treatment system 900. The radiation treatment system 900 is similar to the radiation treatment system 700, including a primary collimator 703 and the integrated, secondary collimator 702 (e.g., having one or two variable-aperture collimators 401 and/or 501 and a fixed-aperture collimator 404 or 504) of the LINAC 701. The radiation treatment system 900 also includes a tool tray 903 that houses multiple (e.g., twelve) fixed-aperture collimators 904. The tool tray 903 includes multiple collimator receptacles that each house one collimator 904.

In one embodiment, the tool tray 903 includes a set of twelve collimator receptacles for holding a set of twelve fixed-aperture collimators. Alternatively, the tool tray 903 may include more or less collimator receptacles than twelve.

In one embodiment, the tool tray 903 includes a keyed cavity that is configured to hold a collimator collar or locking nut. In another embodiment, the tool tray 903 includes one or more light sensitive sensors coupled to the tool tray 903 for calibrating the position of the tool tray 903 with respect to the radiation treatment system 900. For example, the LINAC 701 may generate one or more radiation beams, directed at the light sensitive sensors, and the light sensitive sensors report the position of the tool tray 903 to the controller of the radiation treatment system for calibration purposes. This calibration may allow the radiation treatment robot to position the collimator to engage with the proper collimator receptacle, and in the proper position within the collimator receptacle.

In another embodiment, the collimator receptacle may include a guide mechanism that is configured to engage or disengage a locking mechanism (i.e., retention mechanism) of the collimator housing of the fixed-aperture collimator 904. For example, as the housing of the secondary collimator is lowered to the drop of the fixed-aperture collimator, a retaining pin may be engaged with the guide mechanism and pull the pin, freeing the fixed-aperture collimator 904 to be released from the variable-aperture collimator(s). Alternatively, the guide mechanism may include a ramp to actuate a lock pin (i.e., retention mechanism) to release the fixed-aperture collimator from the secondary collimator housing, allowing the fixed-aperture collimator to be released from the variable-aperture collimator(s).

In another embodiment, the collimator receptacles of the tool tray 903 may have sensors to detect a presence or an absence of each of the collimators 904 in the collimator receptacles, for example, the sensors may be configured to detect that the fixed-aperture collimator 904 is in the center of the collimator receptacle. The collimator receptacles may also have a directional sensor for calibrating the position of the collimator 904 in the collimator receptacle with respect to the radiation treatment system 900. Alternatively, the collimator receptacles may be implemented without the sensors and/or the direction sensors.

In another embodiment, the tool tray 903 includes stress points in the tool tray 903 to allow the tool tray 903 to break before causing damage to the LINAC 701 or robotic arm 703 in the event of contact between the tool tray 903 and the LINAC 701 or robotic arm 703. Alternatively, the tool tray 903 may include light sensitive sensors, proximity sensors, stress points, or any combination thereof.

The robotic arm 703 of the radiation treatment system 900 and the integrated collimator 702 may be configured to switch one of the twelve collimators 904 from a collimator receptacle of the tool tray 903 to be disposed within one or more variable-aperture collimators for coupling the fixed-aperture collimator 904 to the variable-aperture collimator(s). Similarly, the robotic arm 703 of the radiation treatment system 900 and the integrated collimator 702 may be configured to switch one of the twelve collimators 904 from within the collimator housing of the variable-aperture collimator(s) to an empty collimator receptacle of the tool tray 903.

In one embodiment, the radiation treatment system 900 uses the movement of the LINAC 701, manipulated by the robotic arm 703, to automatically change the fixed-aperture collimators 904. The movement of the robotic arm 703 may be coordinated with the opening and closing of one or more variable-aperture collimators. For example, the robotic arm 703 can move the LINAC, including the integrated, secondary collimator 702 from the first position 901 to the second position 902 above one of the collimator receptacles of the tool tray 903, which houses a fixed-aperture collimator 904. The aperture(s) of one or more variable-aperture collimators are opened, using one or more programmable drive mechanisms, and the fixed-aperture collimator 901 is positioned within the open aperture(s) of the one or more variable-aperture collimators of the integrated secondary collimator 702. Once, the fixed-aperture collimator 901 is positioned within the open aperture(s), the one or more programmable drive mechanisms drive the leaves of the variable-aperture collimator(s) to close, retaining the fixed-aperture collimator 901 within the variable-aperture collimator(s). Once the fixed-aperture collimator 901 has been retained within the variable-aperture collimator(s), the robotic arm 703 moves the LINAC 701 away from the tool tray 903. The robotic arm 703 may position the LINAC 701 in a treatment position to direct radiation beams to a target region, such as a target region located with a patient on a treatment couch.

Similarly, the movement of the robotic arm 703 may position the integrated, secondary collimator 702 over an empty collimator receptacle of the tool tray 903. Once the integrated, secondary collimator 702 is above the empty receptacle, the one or more programmable drive mechanisms drive the leaves of the one or more variable-aperture collimators to open the aperture(s), releasing the fixed-aperture collimator 901 into the collimator receptacle of the tool tray 903.

In one embodiment, a user may program the robotic arm 703 to position the integrated, secondary collimator 702 to be positioned in the correct location for picking up and dropping off fixed-aperture collimators 904.

These operations of moving the robotic arm 703, and opening and closing the aperture(s) of the one or more variable-aperture collimators to retain and release the fixed-aperture collimator may be used in connection with additional retention mechanism as described herein. Also, the movement of the integrated, secondary collimator 702 may be used to retain or release a locking nut that is located at the end (e.g., 409 or 512) of the secondary collimator at which the radiation beam exits the secondary collimator (e.g., turning the locking nut approximately a quarter turn to achieve positive locking or turning the locking nut approximately a quarter turn in the other direction to release the locking nut).

Figure 2:
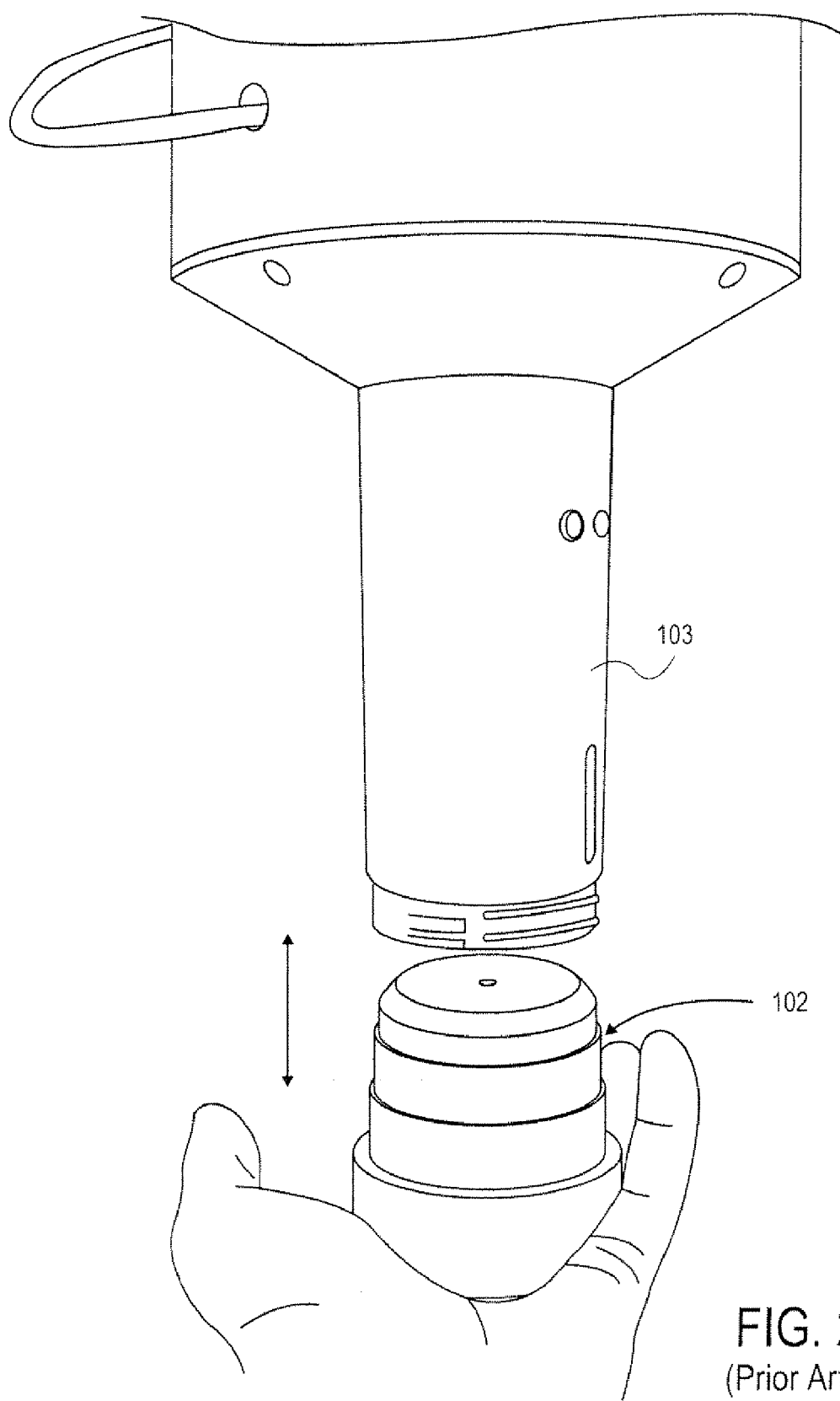
FIG. 2 illustrates a fixed-aperture collimator released from a collimator housing during a manual process of changing a collimator.
Figure 3:
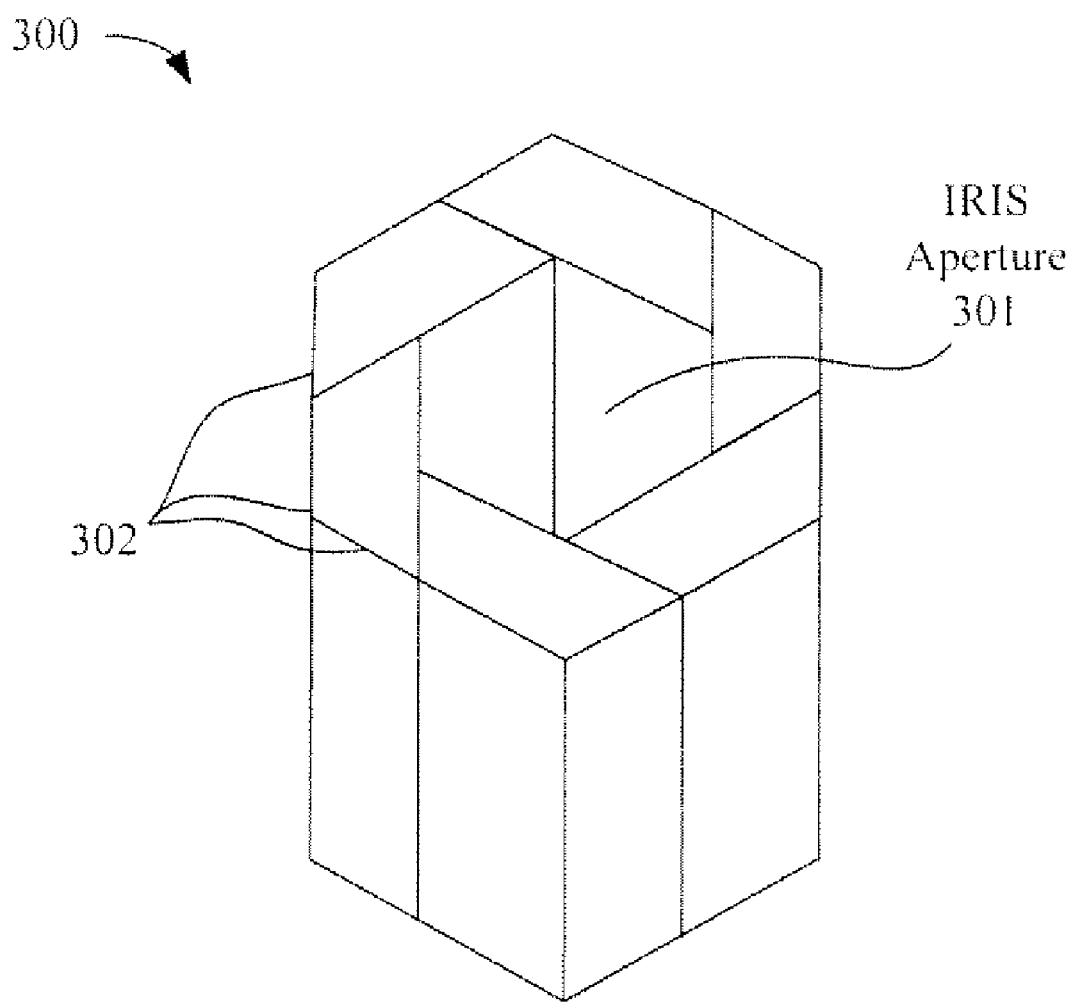
FIG. 3 illustrates an IRIS collimator.

Although the embodiments described with respect to FIGS. 9A and 9B are used for automatically changing the fixed-aperture collimators 904 using the movement of the robotic arm 703 coupled to the LINAC 701, the embodiments described herein may also be used in a radiation treatment system in which the fixed-aperture collimators are manually changed, similar to the manual process described with respect to FIGS. 1 and 2. Also, other types of robots or other types of electro-mechanical devices may be used to position the integrated, secondary collimator 702 for picking up and dropping off the fixed-aperture collimator 904.

Figure 10:
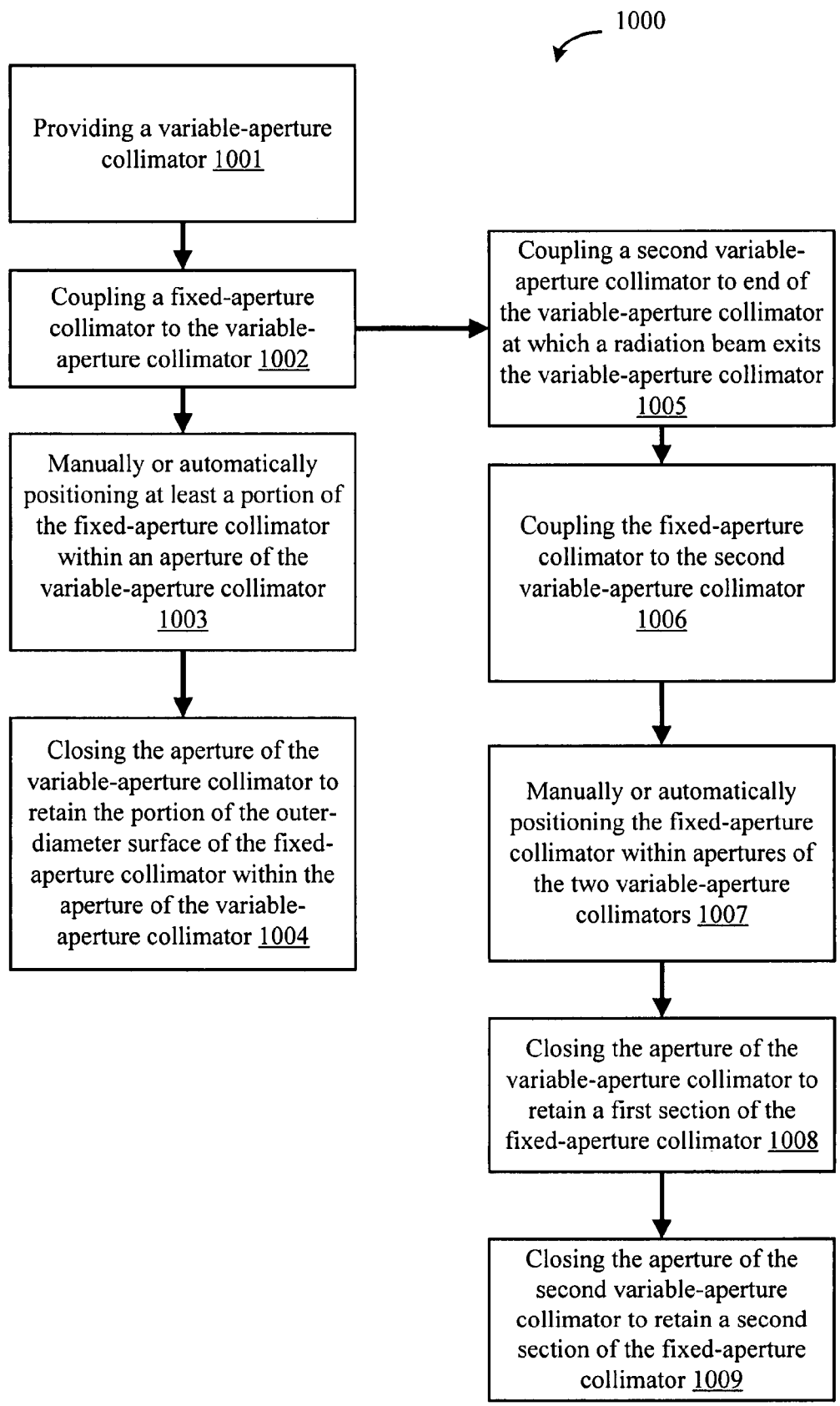
FIG. 10 illustrates a flow chart of one embodiment of a method for coupling a fixed-aperture collimator to a variable-aperture collimator.

FIG. 10 illustrates a flow chart of one embodiment of a method 1000 for coupling a fixed-aperture collimator to a variable-aperture collimator. The method 1000 includes, first, providing the variable-aperture collimator, operation 1001, and second, coupling the fixed-aperture collimator to the variable-aperture collimator, operation 1002. In one embodiment, coupling the fixed-aperture collimator to the variable-aperture collimator in operation 1002, includes manually or automatically positioning at least a portion of the fixed-aperture collimator within an aperture of the variable-aperture collimator, operation 1003. Once the fixed-aperture collimator has been positioned within the aperture of the variable-aperture collimator, the aperture of the variable-aperture collimator is closed to retain the portion of the outer-diameter surface of the fixed-aperture collimator within the aperture of the variable-aperture collimator (e.g., within the inner-diameter surface of the variable-aperture collimator), operation 1004.

In another embodiment, coupling the fixed-aperture collimator to the variable-aperture collimator in operation 1002 includes coupling a second variable-aperture collimator to the end 409 of the first variable-aperture collimator at which the radiation beam exits the first variable-aperture collimator, operation 1005, and coupling at least a portion of the fixed-aperture collimator to the second variable-aperture collimator, operation 1006. It should be noted that in this embodiment, the first variable-aperture collimator is coupled to a first section of the fixed-aperture collimator in operation 1002, and the second variable-aperture collimator is coupled to a second section of the fixed-aperture collimator in the operation 1005. The fixed-aperture collimator is manually or automatically positioned with apertures of both variable-aperture collimators, operation 1007, and then both apertures of the two variable-aperture collimators are closed to retain the first and second sections of the fixed-aperture collimator, operations 1008 and 1009. The opening and closing of the two apertures of the two variable-aperture collimators may be driven by one or more drive mechanisms (e.g., programmable drive mechanisms) either substantially sequentially or substantially simultaneously. The opening and closing of the two apertures of the two variable-aperture collimators may also be synchronized in other patterns.

The operation of coupling the fixed-aperture collimator to either one of the variable-aperture collimators may include retaining the outer-diameter surface of the fixed-aperture collimator within the inner-diameter surface of the variable-aperture collimator. The operation of automatically positioning the fixed-aperture collimator within one or two variable-aperture collimators in operations 1003 or 1007 may include moving the one or two variable-aperture collimators using a robotic arm that is coupled to the one or two variable-aperture collimators. Alternatively, the fixed-aperture collimator may be manually positioned within the one or two variable-aperture collimators.

In another embodiment, the method 1000 further includes aligning the first and second variable-aperture collimators to prevent radiation leakage from a radiation beam received from a radiation source of a LINAC. This may be done by disposing the two variable-aperture collimators so that the gaps between the leaves of the two variable-aperture collimators (e.g., IRIS collimators) are not aligned. This may also be done by having a fixed-aperture collimator that has two sections of different widths, such as illustrated in FIGS. 5B, 5C, 5E, and 5F. When the two variable-aperture collimators are closed to retain the two sections of differing widths, the gaps between the leaves of the two variable-aperture collimators are not aligned.

In another embodiment, the method 1000 may further include automatically changing fixed-aperture collimators within one or two variable-aperture collimators. In this embodiment, the tool tray 903 is populated with multiple fixed-aperture collimators 904. In one operation, the fixed-aperture collimators 904 of the tool tray 903 are arranged in the tool tray so that the fixed-aperture collimators are within reach of the LINAC 701. The method may further include starting a treatment plan where the radiation treatment system checks the required collimator size. If the correct collimator is installed in the collimator housing, the treatment proceeds without interruption. However, if the incorrect collimator is installed, the user is presented with the option to automatically change the collimator, to check again or to abort. Selecting the option to automatically change starts the process of changing the collimator.

The process of changing the collimator may include the following operations. The robotic arm 703 moves the LINAC 701, including the integrated, secondary collimator 702, above a collimator receptacle of the tool tray 903 where the desired fixed-aperture collimator is housed. The system may check to determine if the desired collimator is within the collimator receptacle. The leaves of the one or two variable-aperture collimators are opened. The LINAC 701 is moved toward the collimator receptacle to position the fixed-aperture collimator within the aperture(s) of one or two variable-aperture collimators. Once the fixed-aperture collimator within the collimator receptacle is within the aperture(s) of the one or two variable-aperture collimators, the leaves of the one or two variable-aperture collimators are closed so that the inner-diameter surface of the leaves retain the outer-diameter surface of the fixed-aperture collimator. Once the fixed-aperture collimator is retained within the one or two variable-aperture collimators, the robotic arm 703 moves the LINAC 701 away from the collimator receptacle. After successful exchange the robotic arm 703 may return to a perch position and continue the treatment delivery according to the treatment plan.

The above operations are used to pick up a fixed-aperture collimator using the robotic arm 703. The process of changing the collimator may also include operations to drop off a fixed-aperture collimator using the robotic arm. When dropping off the fixed-aperture collimator, the robotic arm 703 moves the LINAC 701, including the integrated, secondary collimator 702, towards an empty collimator receptacle. Once the integrated collimator 702 is positioned within the empty collimator receptacle, the leaves of the one or two variable-aperture collimators are opened, releasing the fixed-aperture collimator into the collimator receptacle. The robotic arm 703 moves the LINAC 701 away from the collimator receptacle. The system may check to ensure that the collimator 704 is in fact removed.

In other embodiment, the processing of changing the fixed-aperture collimators may include other operations, such as those described below. The system may check to see if the assigned keyed cavity for the collimator collar is empty. If the keyed cavity is not empty, the radiation treatment system may post an error and force a manual change by an operator. In another embodiment, the robotic arm 703 of the radiation treatment system moves the LINAC 701 into the assigned position where it can check the position of the tool tray 903 using the linear accelerator laser. This may be done using one or more light sensitive sensors that are mounted to the tool tray 903. If proper positioning cannot be ascertained, a manual change may be forced. In this operation, the LINAC 701 is subsequently moved over the keyed cavity of the tool tray 903 using the robotic arm 703.

In another embodiment, the robotic arm 703 approaches the tool tray 903, and lowers the LINAC 701, including the integrated, secondary collimator 702, into a keyed cavity, which can house the collimator collar (e.g., locking nut on the collimator housing). The robotic arm 703 turns the LINAC 701, for example, by a quarter turn, to disengage the collimator collar from the collimator housing. The robotic arm 703 retreats from the tool tray 903, leaving the collimator collar in the keyed cavity. Similarly, the robotic arm 703 turns the LINAC 701 in the other direction, for example, by a quarter turn, to engage the collimator housing to the collimator housing.

It should be noted that although discussed at times herein in regards to a robotic-based, image guided radiation treatment system, the methods and apparatus discussed herein may also be used with other types of radiation treatment systems. In alternative embodiments, other types of mechanisms such as a gantry arm or an o-ring with a gimbaled head assembly may be utilized to move a LINAC and, thereby, the integrated collimator.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by the treatment planning system, such as the application of a beam (e.g., radiation, acoustic, etc.) and "target" may refer to a non-anatomical object or area.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner. Additionally, some operations may be repeated within an iteration of a particular method.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
providing a first variable-aperture collimator comprising a plurality of leaves; coupling a fixed-aperture collimator to the first variable-aperture collimator, wherein coupling the fixed-aperture collimator comprises retaining at least a portion of an outer-diameter surface of the fixed-aperture collimator within an inner-diameter surface of the plurality of leaves of the first variable-aperture collimator; and
coupling the first variable-aperture collimator to an end of a primary collimator of a linear accelerator (LINAC) at which a radiation beam is configured to exit the primary collimator, wherein the fixed-aperture collimator and the first variable-aperture collimator form an integrated secondary collimator.

2. The method of claim 1, wherein retaining comprises:
positioning at least a portion of the fixed-aperture collimator within an aperture of the first variable-aperture collimator; and
closing the aperture of the first variable-aperture collimator to retain the portion of the fixed-aperture collimator within the aperture of the first variable-aperture collimator.

3. The method of claim 2, wherein positioning the fixed-aperture collimator comprises automatically positioning the fixed-aperture collimator within the aperture of the first variable-aperture collimator.

4. The method of claim 3, wherein automatically positioning the fixed-aperture collimator comprises moving the first variable-aperture collimator using a robotic arm coupled to the first variable-aperture collimator.

5. The method of claim 2, wherein positioning the fixed-aperture collimator comprise manually positioning the fixed-aperture collimator within the aperture of the first variable-aperture collimator.

6. The method of claim 1, further comprising:
coupling a second variable-aperture collimator to the end of the first variable-aperture collimator at which the radiation beam exits the first variable-aperture collimator, wherein the fixed-aperture collimator, the first variable-aperture collimator, and the second variable-aperture collimator form the integrated secondary collimator;
retaining a first section of the outer-diameter surface of the fixed-aperture collimator within the inner-diameter surface of the first variable-aperture collimator; and
retaining a second section of the outer-diameter surface of the fixed-aperture collimator within the inner-diameter surface of the second variable-aperture collimator.

7. The method of claim 6, wherein coupling the fixed-aperture collimator comprises disposing the first and second variable-aperture collimators to prevent radiation leakage from a radiation beam received from a primary collimator that is coupled to the first variable-aperture collimator.

8. The method of claim 6, wherein retaining the first and second sections of the outer-diameter surface of the fixed-aperture collimator comprises:
   positioning the fixed-aperture collimator within apertures of the first and second variable-aperture collimators;
   closing the aperture of the first variable-aperture collimator to retain the first section of the outer-diameter surface of the fixed-aperture collimator within the inner-diameter surface of the first variable-aperture collimator; and
   closing the aperture of the second variable-aperture collimator to retain the second section of the outer-diameter surface of the fixed-aperture collimator within the inner-diameter surface of the second variable-aperture collimator.

9. The method of claim 8, wherein positioning the fixed-aperture collimator comprise automatically positioning the fixed-aperture collimator within the aperture of the first and second variable-aperture collimators.

10. The method of claim 9, wherein automatically positioning the fixed-aperture collimator comprises moving the first and second variable-aperture collimators using a robotic arm coupled to the first variable-aperture collimator.

11. The method of claim 8, wherein positioning the fixed-aperture collimator comprise manually positioning the fixed-aperture collimator within the aperture of the first and second variable-aperture collimators.

12. The method of claim 8, wherein closing the apertures of the first and second variable-aperture collimators comprises closing the apertures of the first and second variable-aperture collimators either substantially sequentially or substantially simultaneously.

13. An apparatus, comprising:
   a variable-aperture collimator comprising a plurality of leaves; and
   a fixed-aperture collimator coupled to the variable-aperture collimator, wherein at least a portion of the outer-diameter surface of the fixed-aperture collimator is coupled to the inner-diameter surface of the plurality of leaves of the variable-aperture collimator, wherein the variable-aperture collimator is coupled to the end of a primary collimator of a linear accelerator (LINAC) at which a radiation beam is configured to exit the primary collimator, wherein the fixed-aperture collimator and the variable-aperture collimator are an integrated secondary collimator.

14. The apparatus of claim 13, wherein the LINAC is a robot-based LINAC.

15. The apparatus of claim 13, wherein the LINAC is a gantry-based LINAC.

16. The apparatus of claim 13, wherein the variable-aperture collimator is an IRIS collimator, and wherein the plurality of leaves are configured to open and close an aperture of the IRIS collimator.

17. The apparatus of claim 16, wherein the IRIS collimator is a six-sided IRIS collimator and comprises six leaves to open and close the aperture of the IRIS collimator.

18. The apparatus of claim 13, further comprising an additional variable-aperture collimator coupled to the end of the variable-aperture collimator at which the radiation beam exits the variable-aperture collimator, wherein at least another portion of the outer-diameter surface of the fixed-aperture collimator is coupled to the inner-diameter surface of the additional variable-aperture collimator.

19. The apparatus of claim 18, wherein the variable-aperture collimator is a first IRIS collimator having the plurality of leaves configured to open and close an aperture of the first IRIS collimator, wherein the additional variable-aperture collimator is a second IRIS collimator having another plurality of leaves configured to open and close an aperture of the second IRIS collimator, wherein the fixed-aperture collimator has a first section and a second section, wherein the first section is coupled to the first IRIS collimator and the second section is coupled to the second IRIS collimator.

20. The apparatus of claim 18, wherein the fixed-aperture collimator has a first section and a second section, wherein the width of the first section of the fixed-aperture collimator is wider than the width of the second section of the fixed-aperture collimator, and wherein the second section is closer to the end of the additional variable-aperture collimator at which the radiation beam exits the additional variable-aperture collimator than the first section.

21. The apparatus of claim 18, further comprising a first retention mechanism coupled to the additional variable-aperture collimator to retain the fixed-aperture collimator within the additional variable-aperture collimator.

22. The apparatus of claim 21, wherein the first retention mechanism is a stopper.

23. The apparatus of claim 18, further comprising:
   a first drive mechanism coupled to the variable-aperture mechanism configured to open and close an aperture of the variable-aperture collimator; and
   a second drive mechanism coupled to the additional variable-aperture mechanism configured to open and close an aperture of the additional variable-aperture collimator.

24. The apparatus of claim 23, wherein the first and second drive mechanisms are programmable drive mechanisms.

25. The apparatus of claim 13, further comprising a first retention mechanism coupled to the variable-aperture collimator to retain the fixed-aperture collimator within the variable-aperture collimator.

26. The apparatus of claim 25, wherein the first retention mechanism is a stopper.

27. The apparatus of claim 13, wherein the inner-diameter surface of the fixed-aperture collimator has a circular shape about a longitudinal axis, and wherein the outer-diameter surface of the fixed-aperture collimator has a hexagonal shape about the longitudinal axis.

28. The apparatus of claim 13, wherein the outer-diameter surface of the fixed-aperture collimator has at least one of a square, rectangular, pentagonal, octagonal, or hexagonal shape about a longitudinal axis.

29. An apparatus, comprising:
   a variable-aperture collimator;
   a fixed-aperture collimator coupled to the variable-aperture collimator, wherein at least a portion of the outer-diameter surface of the fixed-aperture collimator is coupled to the inner-diameter surface of the variable-aperture collimator, wherein the variable-aperture collimator is coupled to the end of a primary collimator of a linear accelerator (LINAC) at which a radiation beam is configured to exit the primary collimator, wherein the fixed-aperture collimator and the variable-aperture collimator are an integrated secondary collimator; and
   a drive mechanism coupled to the variable-aperture collimator to open and close an aperture of the variable-aperture collimator.

30. The apparatus of claim 29, wherein the drive mechanism is a programmable drive mechanism.

* * * * *